United States Patent
Biederman et al.

(10) Patent No.: US 9,692,230 B2
(45) Date of Patent: *Jun. 27, 2017

(54) DEVICE WITH DUAL POWER SOURCES

(71) Applicant: Verily Life Sciences LLC, Mountain View, CA (US)

(72) Inventors: William James Biederman, Fox Island, WA (US); Nathan Pletcher, Mountain View, CA (US); Andrew Nelson, Richmond, CA (US); Daniel Yeager, Berkeley, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 453 days.

This patent is subject to a terminal disclaimer.

(21) Appl. No.: 14/258,392

(22) Filed: Apr. 22, 2014

(65) Prior Publication Data

US 2015/0076909 A1 Mar. 19, 2015

Related U.S. Application Data

(63) Continuation of application No. 14/028,196, filed on Sep. 16, 2013, now Pat. No. 8,742,623.

(51) Int. Cl.
*H02J 1/10* (2006.01)
*G02C 7/04* (2006.01)
(Continued)

(52) U.S. Cl.
CPC .............. *H02J 1/10* (2013.01); *A61B 5/6821* (2013.01); *G02B 27/017* (2013.01); *G02C 7/04* (2013.01);
(Continued)

(58) Field of Classification Search
CPC . H02J 1/10; G02B 27/017; G02B 2027/0118; G02B 2027/014;
(Continued)

(56) References Cited

U.S. PATENT DOCUMENTS 8,308,707 B2 11/2012 Santini
8,621,245 B2 12/2013 Shearer et al.
(Continued)

FOREIGN PATENT DOCUMENTS

EP 1941829 A2 7/2008
EP 2648031 A1 10/2013
(Continued)

OTHER PUBLICATIONS

International Preliminary Report and Written Opinion for PCT/US2014/035191 mailed Mar. 31, 2016.
(Continued)

*Primary Examiner* — Hal Kaplan
(74) *Attorney, Agent, or Firm* — McDonnell Boehnen Hulbert & Berghoff LLP

(57) ABSTRACT

A wearable device includes a sensor, auxiliary electronics, a primary power supply configured to harvest radio frequency (RF) radiation received from an external reader and use the harvested RF radiation to power the sensor, and an auxiliary power supply configured to harvest energy other than that received from the external reader and use the harvested energy to supply power to the sensor and/or the auxiliary electronics. The external reader may supply less power in response to operation of the auxiliary power supply. Additionally or alternatively, in response to a determination that the auxiliary power supply is unable to supply power, the wearable device may disable all auxiliary electronics but for the sensor. In response to a determination that the primary power supply is unable to supply power but the auxiliary power supply is able to supply power, the wearable device may retain operating parameters in the memory storage unit using the auxiliary power supply.

29 Claims, 9 Drawing Sheets

(51) Int. Cl.
*A61B 5/00* (2006.01)
*G02B 27/01* (2006.01)
*A61B 5/145* (2006.01)

(52) U.S. Cl.
CPC ... *A61B 5/14532* (2013.01); *A61B 2560/0214* (2013.01); *G02B 2027/014* (2013.01); *G02B 2027/0118* (2013.01); *Y10T 307/505* (2015.04); *Y10T 307/696* (2015.04)

(58) Field of Classification Search
CPC .............. A61B 5/6821; A61B 5/14532; A61B 2560/0214; G02C 7/04; Y10T 307/505; Y10T 307/696
USPC ............................. 307/44, 80; 600/319, 345
See application file for complete search history.

(56) References Cited

U.S. PATENT DOCUMENTS

| | | | |
|---|---|---|---|
| 8,742,623 B1* | 6/2014 | Biederman | G02B 27/017 307/80 |
| 9,133,024 B2 | 9/2015 | Phan | |
| 9,192,772 B1* | 11/2015 | Tsukamoto | A61N 1/3787 |
| 9,523,865 B2* | 12/2016 | Pletcher | G02C 7/04 |
| 2002/0049389 A1 | 4/2002 | Abreu | |
| 2004/0116794 A1 | 6/2004 | Fink et al. | |
| 2004/0242976 A1 | 12/2004 | Abreu | |
| 2006/0281435 A1 | 12/2006 | Shearer et al. | |
| 2008/0076974 A1 | 3/2008 | Yamazaki et al. | |
| 2008/0091090 A1 | 4/2008 | Guillory et al. | |
| 2008/0139953 A1 | 6/2008 | Baker et al. | |
| 2009/0118604 A1 | 5/2009 | Phan et al. | |
| 2010/0090656 A1 | 4/2010 | Shearer et al. | |
| 2010/0191072 A1 | 7/2010 | Matsumori et al. | |
| 2011/0040161 A1 | 2/2011 | Abreu | |
| 2011/0084834 A1 | 4/2011 | Sabeta | |
| 2012/0068848 A1 | 3/2012 | Campbell et al. | |
| 2012/0245444 A1 | 9/2012 | Otis et al. | |
| 2012/0259188 A1 | 10/2012 | Besling | |
| 2012/0271121 A1 | 10/2012 | Della Torre et al. | |

FOREIGN PATENT DOCUMENTS

| | | |
|---|---|---|
| WO | 2009/059203 A1 | 5/2009 |
| WO | 2010/033679 A2 | 3/2010 |
| WO | 2011/163080 A1 | 12/2011 |

OTHER PUBLICATIONS

Scott Calabrese Barton et al., "Enzymatic Biofuel Cells for Implantable and Microscale Devices," Chemical Reviews, 2004, vol. 104, pp. 4867-4886.

Magnus Falk et al: "Miniature Biofuel Cell as a Potential Power Source for Glucose-Sensing Contact Lenses", Analytical Chemistry, vol. 85, No. 13, Jul. 2, 2013, pp. 6342-6348, XP055337370, US ISSN: 0003-2700, DOI: 10.1021/ac4006793.

Magnus Falk et al: "Biofuel cell as a power source for electronic contact lenses", Biosensors and Bioelectronics, Elsevier BV, NL, vol. 37, No. 1, Apr. 17, 2012, pp. 38-45, XP028517358, ISSN: 0956-5663, DOI: 10.1016/J.BIOS.2012.04.030.

Extended European Search Report, dated Mar. 30, 2017, in European Patent Application No. 14844445.8.

* cited by examiner

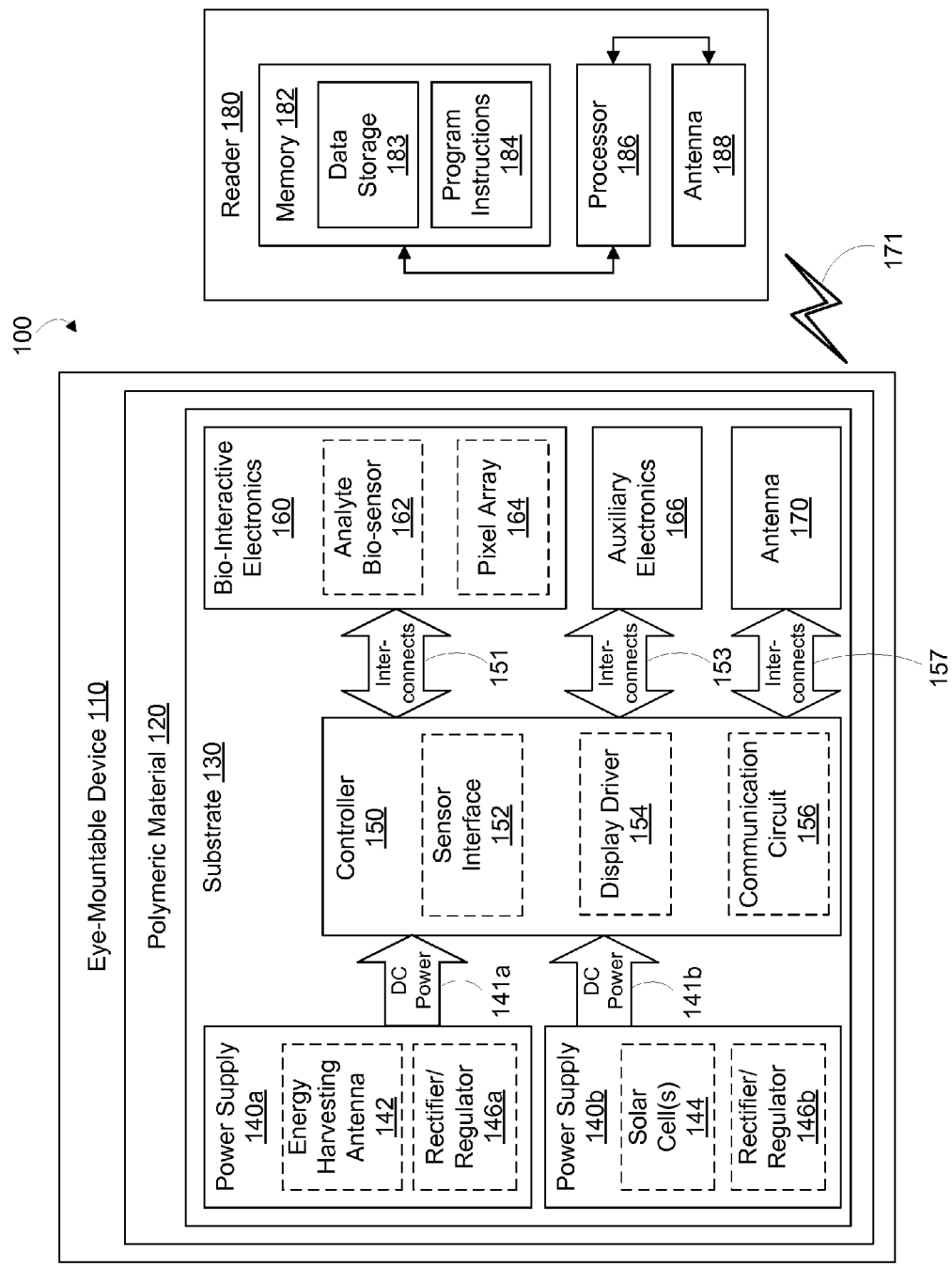

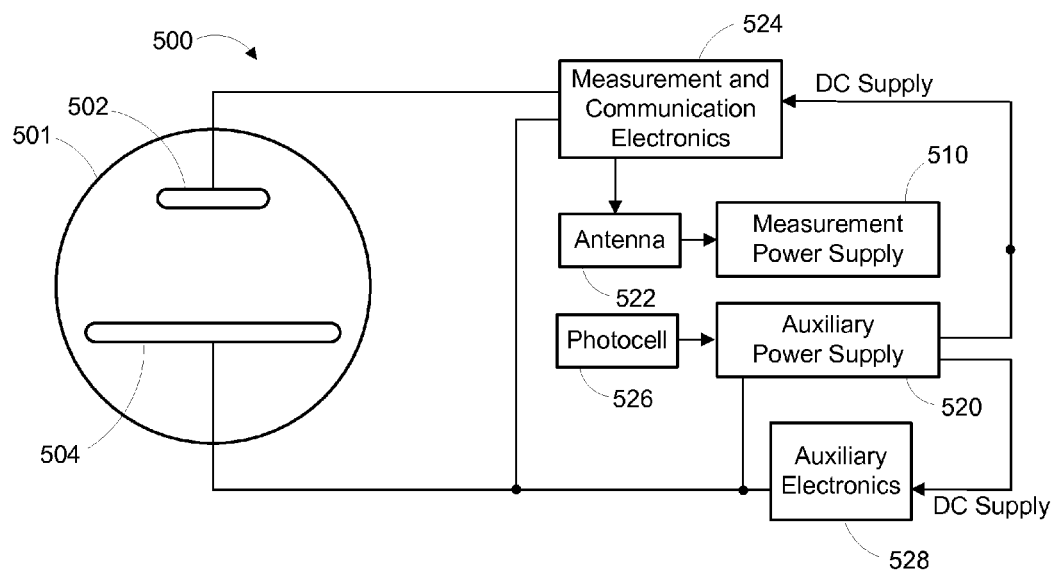
FIG. 5A
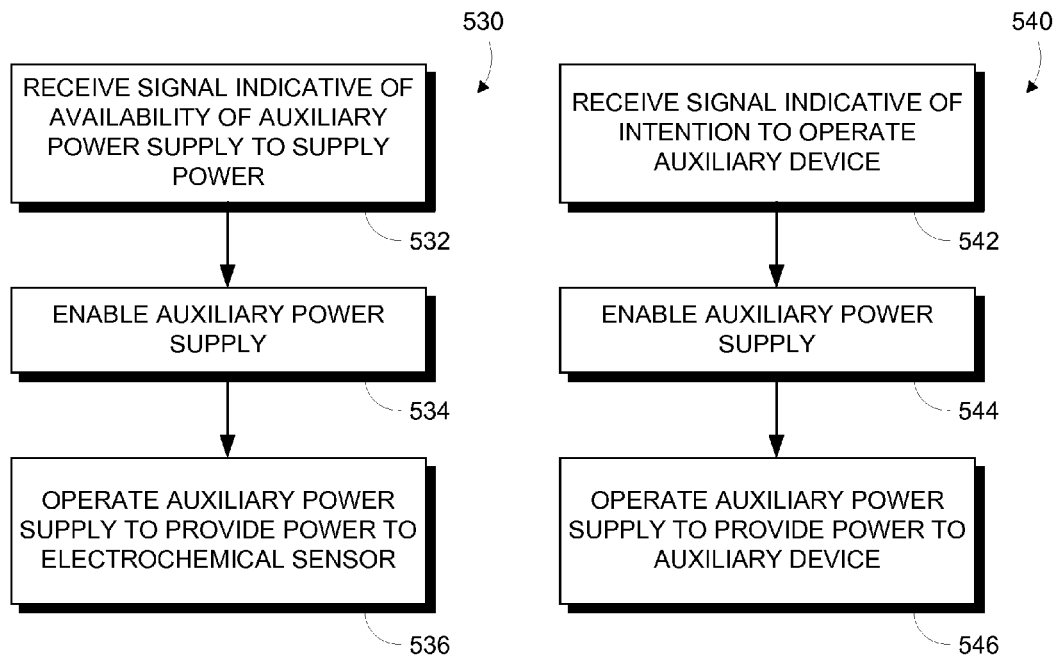
FIG. 5B  FIG. 5C

DEVICE WITH DUAL POWER SOURCES

BACKGROUND

Unless otherwise indicated herein, the materials described in this section are not prior art to the claims in this application and are not admitted to be prior art by inclusion in this section.

An electrochemical amperometric sensor measures a concentration of an analyte by measuring a current generated through electrochemical oxidation or reduction reactions of the analyte at a working electrode of the sensor. A reduction reaction occurs when electrons are transferred from the electrode to the analyte, whereas an oxidation reaction occurs when electrons are transferred from the analyte to the electrode. The direction of the electron transfer is dependent upon the electrical potentials applied to the working electrode. A counter electrode and/or reference electrode is used to complete a circuit with the working electrode and allow the generated current to flow. When the working electrode is appropriately biased, the output current can be proportional to the reaction rate, so as to provide a measure of the concentration of the analyte surrounding the working electrode.

In some examples, a reagent is localized proximate the working electrode to selectively react with a desired analyte. For example, glucose oxidase can be fixed near the working electrode to react with glucose and release hydrogen peroxide, which is then electrochemically detected by the working electrode to indicate the presence of glucose. Other enzymes and/or reagents can be used to detect other analytes.

SUMMARY

Some embodiments of the present disclosure provide a method that includes a wearable device receiving a signal indicative of an availability of an auxiliary power supply to provide power to the wearable device. The wearable device may include: at least one sensor, a primary power supply configured to harvest radio frequency (RF) radiation received from an external reader and use the harvested RF radiation to power the at least one sensor, and an auxiliary power supply configured to harvest energy other than that received from the external reader and use the harvested energy to supply power to the at least one sensor. The method may further include receiving a signal indicative of an availability of the auxiliary power supply to provide power to the wearable device, and responsive to receiving the signal, the wearable device enabling the auxiliary power supply. The method may further include the wearable device operating the auxiliary power supply to supply power to the at least one sensor.

Some embodiments of the present disclosure provide a wearable device that includes a sensor, an antenna, and auxiliary electronics, including a memory storage unit. The wearable device may further include a first power supply configured to harvest radio frequency (RF) radiation received at the antenna from an external reader and a second power supply configured to harvest energy other than that received from the external reader. Each power supply is configured to supply power to the sensor and the auxiliary electronics. The wearable device may further include a controller electrically connected to the first power supply and the second power supply. In some embodiments, the controller can be configured to: enable the second power supply in response to a determination that the second power supply is able to supply power, disable all auxiliary electronics but for the sensor in response to a determination that the second power supply is unable to supply power, and retain operating parameters in the memory storage unit using the second power supply in response to a determination that the first power supply is unable to supply power but the second power supply is able to supply power.

Some embodiments of the present disclosure provide a non-transitory computer readable medium (CRM) having instructions stored thereon that, when executed by one or more processors associated with a wearable device, cause the wearable device to perform operations. Such operations may include receiving a signal indicative of an availability of an auxiliary power supply to provide power to the wearable device. The wearable device may include at least one sensor, a primary power supply configured to harvest radio frequency (RF) radiation received from an external reader and use the harvested RF radiation to power at least one sensor, and an auxiliary power supply configured to harvest energy other than that received from the external reader and use the harvested energy to supply power to the at least one sensor. The operations may further include responsive to receiving the signal, enabling the auxiliary power supply, and operating the auxiliary power supply to supply power to the at least one sensor.

These as well as other aspects, advantages, and alternatives, will become apparent to those of ordinary skill in the art by reading the following detailed description, with reference where appropriate to the accompanying figures.

BRIEF DESCRIPTION OF THE FIGURES

FIG. 1 is a block diagram of an example system that includes an eye-mountable device in wireless communication with an external reader, in accordance with one embodiment.

FIG. 5A is a functional block diagram of an example electrochemical sensor system including dual power supplies, in accordance with one embodiment.

FIG. 5B is a flowchart of an example process for operating the example electrochemical sensor of FIG. 5A, in accordance with one embodiment.

FIG. 5C is a flowchart of an example process for operating the example electrochemical sensor of FIG. 5A, in accordance with one embodiment.

DETAILED DESCRIPTION

Figure 2A:
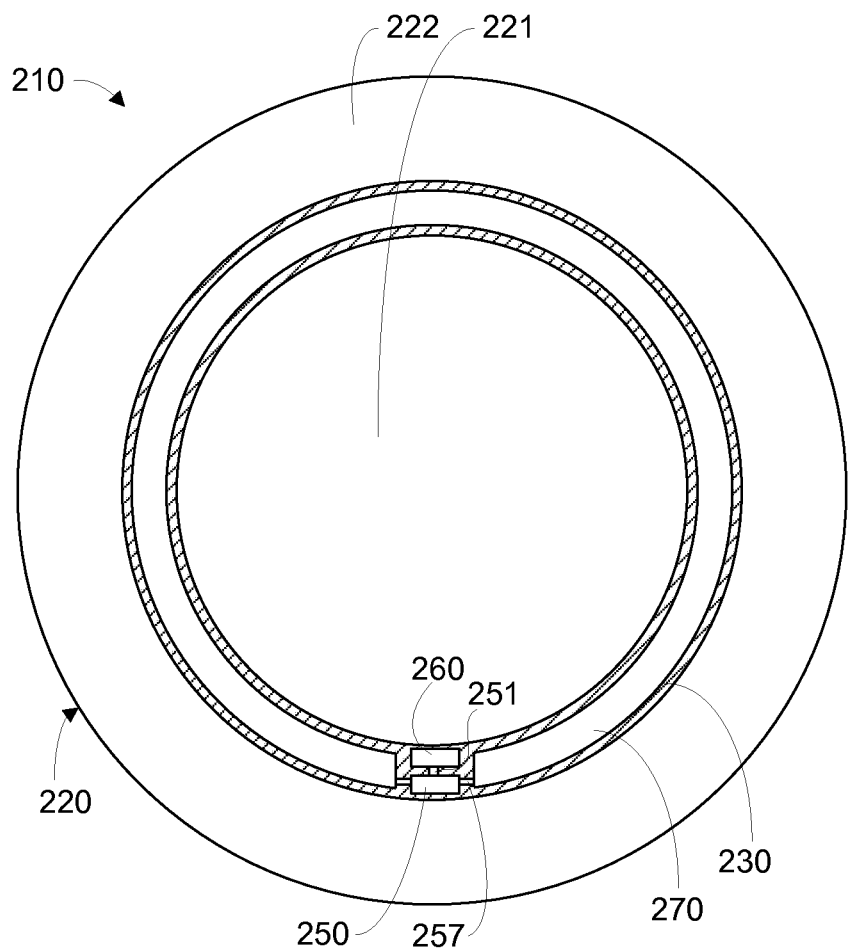
FIG. 2A is a bottom view of an example eye-mountable device, in accordance with one embodiment.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

An ophthalmic sensing platform or implantable sensing platform can include a sensor, control electronics and an antenna all situated on a substrate embedded in a polymeric material. The polymeric material can be incorporated in an ophthalmic device, such as an eye-mountable device or an implantable medical device. The control electronics can operate the sensor to perform readings and can operate the antenna to wirelessly communicate the readings from the sensor to an external reader via the antenna.

In some examples, the polymeric material can be in the form of a round lens with a concave curvature configured to mount to a corneal surface of an eye. The substrate can be embedded near the periphery of the polymeric material to avoid interference with incident light received closer to the central region of the cornea. The sensor can be arranged on the substrate to face inward, toward the corneal surface, so as to generate clinically relevant readings from near the surface of the cornea and/or from tear fluid interposed between the polymeric material and the corneal surface. Additionally or alternatively, the sensor can be arranged on the substrate to face outward, away from the corneal surface and toward the layer of tear fluid coating the surface of the polymeric material exposed to the atmosphere. In some examples, the sensor is entirely embedded within the polymeric material. For example, an electrochemical sensor that includes a working electrode and a reference electrode can be embedded in the polymeric material and situated such that the sensor electrodes are less than 10 micrometers from the polymeric surface configured to mount to the cornea. The sensor can generate an output signal indicative of a concentration of an analyte that diffuses through the lens material to the sensor electrodes.

The ophthalmic sensing platform can be powered via radiated energy harvested at the sensing platform. Power can be provided by light energizing photovoltaic cells included on the sensing platform. Additionally or alternatively, power can be provided by radio frequency energy harvested from the antenna. A rectifier and/or regulator can be incorporated with the control electronics to generate a stable DC voltage to power the sensing platform from the harvested energy. The antenna can be arranged as a loop of conductive material with leads connected to the control electronics. In some embodiments, such a loop antenna can also wirelessly communicate the sensor readings to an external reader by modifying the impedance of the loop antenna so as to modify backscatter radiation from the antenna.

Tear fluid contains a variety of inorganic electrolytes (e.g., $Ca^{2+}$, $Mg^{2+}$, $Cl^-$, organic components (e.g., glucose, lactate, proteins, lipids, etc.), and so on that can be used to diagnose health states. An ophthalmic sensing platform configured to measure one or more of these analytes can thus provide a convenient non-invasive platform useful in diagnosing and/or monitoring health states. For example, an ophthalmic sensing platform can be configured to sense glucose and can be used by diabetic individuals to measure/monitor their glucose levels.

The sensing platform can be powered by an energy harvesting system to capture energy from incident radiation, rather than by internal energy storage devices requiring more space. For example, power can be provided by light energizing photovoltaic cells included on the sensing platform. Power may also be provided by radio frequency (RF) energy harvested via a loop antenna. A rectifier and/or regulator can be incorporated with the control electronics to generate a stable DC voltage to power the sensing platform from the harvested RF energy. Furthermore, the control electronics can wirelessly communicate the sensor readings to an external reader by modifying the impedance of the loop antenna so as to characteristically modify the backscatter from the antenna.

II. Example Ophthalmic Electronics Platform

FIG. 1 is a block diagram of a system 100 that includes an eye-mountable device 110 in wireless communication with an external reader 180. The exposed regions of the eye-mountable device 110 are made of a polymeric material 120 formed to be contact-mounted to a corneal surface of an eye. A substrate 130 is embedded in the polymeric material 120 to provide a mounting surface for a power supplies 140a and 14b, a controller 150, bio-interactive electronics 160, and a communication antenna 170. The bio-interactive electronics 160 are operated by the controller 150. Power supplies 140a and 140b supply operating voltages to the controller 150 and/or the bio-interactive electronics 160. The antenna 170 is operated by the controller 150 to communicate information to and/or from the eye-mountable device 110. The antenna 170, the controller 150, power supply 140a, power supply 140b, and the bio-interactive electronics 160 can all be situated on the embedded substrate 130. Because the eye-mountable device 110 includes electronics and is configured to be contact-mounted to an eye, it is also referred to herein as an ophthalmic electronics platform.

To facilitate contact-mounting, the polymeric material 120 can have a concave surface configured to adhere ("mount") to a moistened corneal surface (e.g., by capillary forces with a tear film coating the corneal surface). Additionally or alternatively, the eye-mountable device 110 can be adhered by a vacuum force between the corneal surface and the polymeric material due to the concave curvature. While mounted with the concave surface against the eye, the outward-facing surface of the polymeric material 120 can have a convex curvature that is formed to not interfere with eye-lid motion while the eye-mountable device 110 is mounted to the eye. For example, the polymeric material 120 can be a substantially transparent curved polymeric disk shaped similarly to a contact lens.

The polymeric material 120 can include one or more biocompatible materials, such as those employed for use in contact lenses or other ophthalmic applications involving direct contact with the corneal surface. The polymeric material 120 can optionally be formed in part from such biocompatible materials or can include an outer coating with such biocompatible materials. The polymeric material 120 can include materials configured to moisturize the corneal surface, such as hydrogels and the like. In some embodiments, the polymeric material 120 can be a deformable ("non-rigid") material to enhance wearer comfort. In some embodiments, the polymeric material 120 can be shaped to provide a predetermined, vision-correcting optical power, such as can be provided by a contact lens.

The substrate 130 includes one or more surfaces suitable for mounting the bio-interactive electronics 160, the controller 150, the power supplies 140a and 140b, and the antenna 170. The substrate 130 can be employed both as a mounting platform for chip-based circuitry (e.g., by flip-chip mounting to connection pads) and/or as a platform for patterning conductive materials (e.g., gold, platinum, palladium, titanium, copper, aluminum, silver, metals, other conductive materials, combinations of these, etc.) to create electrodes, interconnects, connection pads, antennae, etc. In some embodiments, substantially transparent conductive materials (e.g., indium tin oxide) can be patterned on the substrate 130 to form circuitry, electrodes, etc. For example, the antenna 170 can be formed by forming a pattern of gold or another conductive material on the substrate 130 by deposition, photolithography, electroplating, etc. Similarly, interconnects 151, 157 between the controller 150 and the bio-interactive electronics 160, and between the controller 150 and the antenna 170, respectively, can be formed by depositing suitable patterns of conductive materials on the substrate 130. A combination of microfabrication techniques including, without limitation, the use of photoresists, masks, deposition techniques, and/or plating techniques can be employed to pattern materials on the substrate 130. The substrate 130 can be a relatively rigid material, such as polyethylene terephthalate ("PET") or another material configured to structurally support the circuitry and/or chip-based electronics within the polymeric material 120. The eye-mountable device 110 can alternatively be arranged with a group of unconnected substrates rather than a single substrate. For example, the controller 150 and a bio-sensor or other bio-interactive electronic component can be mounted to one substrate, while the antenna 170 is mounted to another substrate and the two can be electrically connected via the interconnects 157.

In some embodiments, the bio-interactive electronics 160 (and the substrate 130) can be positioned away from the center of the eye-mountable device 110 and thereby avoid interference with light transmission to the central, light-sensitive region of the eye. For example, where the eye-mountable device 110 is shaped as a concave-curved disk, the substrate 130 can be embedded around the periphery (e.g., near the outer circumference) of the disk. In some embodiments, however, the bio-interactive electronics 160 (and the substrate 130) can be positioned in or near the central region of the eye-mountable device 110. Additionally or alternatively, the bio-interactive electronics 160 and/or substrate 130 can be substantially transparent to incoming visible light to mitigate interference with light transmission to the eye. Moreover, in some embodiments, the bio-interactive electronics 160 can include a pixel array 164 that emits and/or transmits light to be received by the eye according to display instructions. Thus, the bio-interactive electronics 160 can optionally be positioned in the center of the eye-mountable device so as to generate perceivable visual cues to a wearer of the eye-mountable device 110, such as by displaying information (e.g., characters, symbols, flashing patterns, etc.) on the pixel array 164.

The substrate 130 can be shaped as a flattened ring with a radial width dimension sufficient to provide a mounting platform for the embedded electronics components. The substrate 130 can have a thickness sufficiently small to allow the substrate 130 to be embedded in the polymeric material 120 without influencing the profile of the eye-mountable device 110. The substrate 130 can have a thickness sufficiently large to provide structural stability suitable for supporting the electronics mounted thereon. For example, the substrate 130 can be shaped as a ring with a diameter of about 10 millimeters, a radial width of about 1 millimeter (e.g., an outer radius 1 millimeter larger than an inner radius), and a thickness of about 50 micrometers. The substrate 130 can optionally be aligned with the curvature of the eye-mounting surface of the eye-mountable device 110 (e.g., convex surface). For example, the substrate 130 can be shaped along the surface of an imaginary cone between two circular segments that define an inner radius and an outer radius. In such an example, the surface of the substrate 130 along the surface of the imaginary cone defines an inclined surface that is approximately aligned with the curvature of the eye mounting surface at that radius.

Power supply 140a is configured to harvest energy to power the controller 150 and bio-interactive electronics 160. For example, a radio-frequency energy-harvesting antenna 142 can capture energy from incident radio radiation. The energy harvesting antenna 142 can optionally be a dual-purpose antenna that is also used to communicate information to the external reader 180. That is, the functions of the communication antenna 170 and the energy harvesting antenna 142 can be accomplished with the same physical antenna.

Power supply 140b is also configured to harvest energy to power the controller 150 and bio-interactive electronics 160; however, power supply 140b is configured to harvest ambient energy other than incident radio radiation. For example, in the embodiment depicted in FIG. 1, power supply 140b may include solar cell(s) 144 ("photovoltaic cells") that can capture energy from incoming ultraviolet, visible, and/or infrared radiation. However, in other embodiments, other types of power sources can be used. For instance, in one example embodiment, power supply 140b may include an inertial power scavenging system that captures energy from ambient vibrations. In another example embodiment, power supply 140b may include a biofuel cell that generates electrical energy in response to chemical reactions occurring at the bio fuel cell. Tear fluid may be used as the fuel for such chemical reactions, although other fuels are possible as well. Alternatively or additionally, power supply 140b may include one or more charge storage devices, such as rechargeable batteries or capacitor arrangements. Other types of power supplies are possible as well.

Rectifier/regulators 146a and 146b can be used to condition the captured energy to stable DC supply voltages 141a and 141b that are supplied to the controller 150. For example, the energy harvesting antenna 142 can receive incident radio frequency radiation. Varying electrical signals on the leads of the antenna 142 are output to the rectifier/regulator 146a. The rectifier/regulator 146a rectifies the varying electrical signals to a DC voltage and regulates the rectified DC voltage to a level suitable for operating the controller 150. Additionally, output voltage from the solar cell(s) 144 or other types of energy capture/storage devices can be regulated to a level suitable for operating the controller 150. The rectifier/regulator 146a and 146b can itself include one or more energy storage devices to mitigate high frequency variations in the ambient energy gathering antenna 142 and/or solar cell(s) 144. For example, one or more energy storage devices (e.g., a capacitor, an inductor, etc.) can be connected in parallel across the outputs of the rectifier 146a and/or 146b to regulate the DC supply voltages 141a and 141b and configured to function as a low-pass filter.

Additionally or alternatively, power supply 140b may include a DC-DC converter that may convert a larger (or smaller) voltage supplied from photovoltaic cells 144, an inertial power scavenging system, a bio fuel cell, and/or a charge storage device, as the case may be, to a more suitable unregulated voltage. In one example, the DC-DC converter may convert a 5V DC supply to 1.2V DC, thereby yielding additional power savings before it is regulated. Other examples of voltage conversion are possible as well.

The controller 150 is turned on when the DC supply voltage 141a or 141b is provided to the controller 150, and the logic in the controller 150 operates the bio-interactive electronics 160 and the antenna 170. The controller 150 can include logic circuitry configured to operate the bio-interactive electronics 160 so as to interact with a biological environment of the eye-mountable device 110. The interaction could involve the use of one or more components, such an analyte bio-sensor 162, in bio-interactive electronics 160 to obtain input from the biological environment. Additionally or alternatively, the interaction could involve the use of one or more components, such as pixel array 164, to provide an output to the biological environment.

In one example, the controller 150 includes a sensor interface module 152 that is configured to operate analyte bio-sensor 162. The analyte bio-sensor 162 can be, for example, an amperometric electrochemical sensor that includes a working electrode and a reference electrode. A voltage can be applied between the working and reference electrodes to cause an analyte to undergo an electrochemical reaction (e.g., a reduction and/or oxidation reaction) at the working electrode. The electrochemical reaction can generate an amperometric current that can be measured through the working electrode. The amperometric current can be dependent on the analyte concentration. Thus, the amount of the amperometric current that is measured through the working electrode can provide an indication of analyte concentration. In some embodiments, the sensor interface module 152 can be a potentiostat configured to apply a voltage difference between working and reference electrodes while measuring a current through the working electrode.

The controller 150 can optionally include a display driver module 154 for operating a pixel array 164. The pixel array 164 can be an array of separately programmable light transmitting, light reflecting, and/or light emitting pixels arranged in rows and columns. The individual pixel circuits can optionally include liquid crystal technologies, micro-electromechanical technologies, emissive diode technologies, etc. to selectively transmit, reflect, and/or emit light according to information from the display driver module 154. Such a pixel array 164 can also optionally include more than one color of pixels (e.g., red, green, and blue pixels) to render visual content in color. The display driver module 154 can include, for example, one or more data lines providing programming information to the separately programmed pixels in the pixel array 164 and one or more addressing lines for setting groups of pixels to receive such programming information. Such a pixel array 164 situated on the eye can also include one or more lenses to direct light from the pixel array to a focal plane perceivable by the eye.

The controller 150 can also include a communication circuit 156 for sending and/or receiving information via the antenna 170. The communication circuit 156 can optionally include one or more oscillators, mixers, frequency injectors, etc. to modulate and/or demodulate information on a carrier frequency to be transmitted and/or received by the antenna 170. In some examples, the eye-mountable device 110 is configured to indicate an output from a bio-sensor by modulating an impedance of the antenna 170 in a manner that is perceivable by the external reader 180. For example, the communication circuit 156 can cause variations in the amplitude, phase, and/or frequency of backscatter radiation from the antenna 170, and such variations can be detected by the reader 180.

The controller 150 is connected to the bio-interactive electronics 160 via interconnects 151. For example, where the controller 150 includes logic elements implemented in an integrated circuit to form the sensor interface module 152 and/or display driver module 154, a patterned conductive material (e.g., gold, platinum, palladium, titanium, copper, aluminum, silver, metals, combinations of these, etc.) can connect a terminal on the chip to the bio-interactive electronics 160. Similarly, the controller 150 is connected to the antenna 170 via interconnects 157.

The controller 150 can also include logic configured to couple to and operate other auxiliary electronics 166 that may be mounted on substrate 130. For instance, auxiliary electronics 166 can include a radio transceiver, configured to communicate via Bluetooth, WiFi, cellular, or another type of communications protocol. Additionally or alternatively, auxiliary electronics 166 can include a type of memory storage, such a volatile or non-volatile memory. Other types of auxiliary electronics are possible as well. Controller 150 is connected to the auxiliary electronics via interconnects 153.

It is noted that the block diagram shown in FIG. 1 is described in connection with functional modules for convenience in description. However, embodiments of the eye-mountable device 110 can be arranged with one or more of the functional modules ("sub-systems") implemented in a single chip, integrated circuit, and/or physical component. For example, while rectifier/regulators 146a and 146b are illustrated in power supply blocks 140a and 14b, respectively, the rectifier/regulators 146a and 146b can be implemented in a chip that also includes the logic elements of the controller 150 and/or other features of the embedded electronics in the eye-mountable device 110. Thus, the DC supply voltage 141a or 141b that is provided to the controller 150 from power supplies 140a or 140b can be a supply voltage that is provided to components on a chip by rectifier and/or regulator components located on the same chip. That is, the functional blocks in FIG. 1 shown as the power supply blocks 140a and 140b and controller block 150 need not be implemented as physically separated modules. Moreover, one or more of the functional modules described in FIG. 1 can be implemented by separately packaged chips electrically connected to one another.

Additionally or alternatively, the energy harvesting antenna 142 and the communication antenna 170 can be implemented with the same physical antenna. For example, a loop antenna can both harvest incident radiation for power generation and communicate information via backscatter radiation.

The external reader 180 includes an antenna 188 (or a group of more than one antennae) to send and receive wireless signals 171 to and from the eye-mountable device 110. The external reader 180 also includes a computing system with a processor 186 in communication with a memory 182. The memory 182 is a non-transitory computer-readable medium that can include, without limitation, magnetic disks, optical disks, organic memory, and/or any other volatile (e.g. RAM) or non-volatile (e.g. ROM) storage system readable by the processor 186. The memory 182 can include a data storage 183 to store indications of data, such as sensor readings (e.g., from the analyte bio-sensor 162), program settings (e.g., to adjust behavior of the eye-mountable device 110 and/or external reader 180), etc. The memory 182 can also include program instructions 184 for execution by the processor 186 to cause the external reader 180 to perform processes specified by the instructions 184. For example, the program instructions 184 can cause external reader 180 to provide a user interface that allows for retrieving information communicated from the eye-mountable device 110 (e.g., sensor outputs from the analyte bio-sensor 162). The external reader 180 can also include one or more hardware components for operating the antenna 188 to send and receive the wireless signals 171 to and from the eye-mountable device 110. For example, oscillators, frequency injectors, encoders, decoders, amplifiers, filters, etc. can drive the antenna 188 according to instructions from the processor 186.

The external reader 180 can be a smart phone, digital assistant, or other portable computing device with wireless connectivity sufficient to provide the wireless communication link 171. The external reader 180 can also be implemented as an antenna module that can be plugged in to a portable computing device, such as in an example where the communication link 171 operates at carrier frequencies not commonly employed in portable computing devices. In some instances, the external reader 180 is a special-purpose device configured to be worn relatively near a wearer's eye to allow the wireless communication link 171 to operate with a low power budget. For example, the external reader 180 can be integrated in a piece of jewelry such as a necklace, earring, etc. or integrated in an article of clothing worn near the head, such as a hat, headband, etc.

In some embodiments, the system 100 can operate to non-continuously ("intermittently") supply energy to the eye-mountable device 110 to power the controller 150 and electronics 160. For example, radio frequency radiation 171 can be supplied to power the eye-mountable device 110 long enough to carry out a tear film analyte concentration measurement and communicate the results. For example, the supplied radio frequency radiation can provide sufficient power to apply a potential between a working electrode and a reference electrode sufficient to induce electrochemical reactions at the working electrode, measure the resulting amperometric current, and modulate the antenna impedance to adjust the backscatter radiation in a manner indicative of the measured amperometric current. In such an example, the supplied radio frequency radiation 171 can be considered an interrogation signal from the external reader 180 to the eye-mountable device 110 to request a measurement. By periodically interrogating the eye-mountable device 110 (e.g., by supplying radio frequency radiation 171 to temporarily turn the device on) and storing the sensor results (e.g., via the data storage 183), the external reader 180 can accumulate a set of analyte concentration measurements over time without continuously powering the eye-mountable device 110.

Further, some embodiments of the system may include privacy controls which may be automatically implemented or controlled by the wearer of the device. For example, in embodiments in which a wearer's collected physiological parameter data and health state data are uploaded to a cloud computing network for trend analysis by a clinician, the data may be treated in one or more ways before it is stored or used, so that personally identifiable information is removed. For example, a wearer's identity may be treated so that no personally identifiable information can be determined for the wearer, or a wearer's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a wearer's preferences, or a wearer's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

Figure 2B:
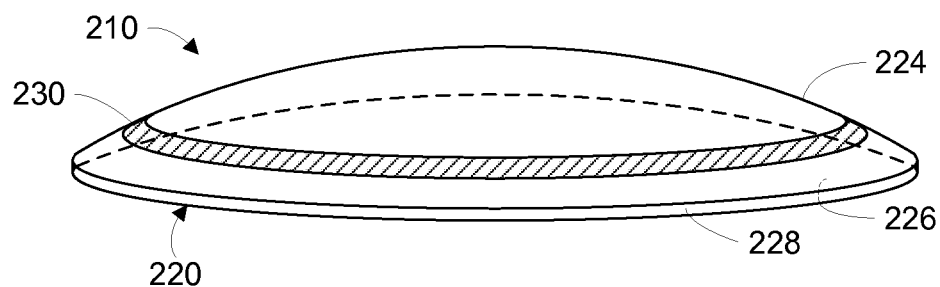
FIG. 2B is a side view of the example eye-mountable device shown in FIG. 2A, in accordance with one embodiment.

FIG. 2A is a bottom view of an example eye-mountable electronic device 210 (or ophthalmic electronics platform). FIG. 2B is an aspect view of the example eye-mountable electronic device shown in FIG. 2A. It is noted that relative dimensions in FIGS. 2A and 2B are not necessarily to scale, but have been rendered for purposes of explanation only in describing the arrangement of the example eye-mountable electronic device 210. The eye-mountable device 210 is formed of a polymeric material 220 shaped as a curved disk. The polymeric material 220 can be a substantially transparent material to allow incident light to be transmitted to the eye while the eye-mountable device 210 is mounted to the eye. The polymeric material 220 can be a biocompatible material similar to those employed to form vision correction and/or cosmetic contact lenses in optometry, such as polyethylene terephthalate ("PET"), polymethyl methacrylate ("PMMA"), polyhydroxyethylmethacrylate ("poly-HEMA"), silicone hydrogels, combinations of these, etc. The polymeric material 220 can be formed with one side having a concave surface 226 suitable to fit over a corneal surface of an eye. The opposite side of the disk can have a convex surface 224 that does not interfere with eyelid motion while the eye-mountable device 210 is mounted to the eye. A circular outer side edge 228 connects the concave surface 224 and convex surface 226.

The eye-mountable device 210 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of the eye-mountable device 210 can be selected according to the size and/or shape of the corneal surface of the wearer's eye.

The polymeric material 220 can be formed with a curved shape in a variety of ways. For example, techniques similar to those employed to form vision-correction contact lenses, such as heat molding, injection molding, spin casting, etc. can be employed to form the polymeric material 220. While the eye-mountable device 210 is mounted in an eye, the convex surface 224 faces outward to the ambient environment while the concave surface 226 faces inward, toward the corneal surface. The convex surface 224 can therefore be considered an outer, top surface of the eye-mountable device 210 whereas the concave surface 226 can be considered an inner, bottom surface. The "bottom" view shown in FIG. 2A is facing the concave surface 226. From the bottom view shown in FIG. 2A, the outer periphery 222, near the outer circumference of the curved disk is curved to extend out of the page, whereas the central region 221, near the center of the disk is curved to extend into the page.

A substrate 230 is embedded in the polymeric material 220. The substrate 230 can be embedded to be situated along the outer periphery 222 of the polymeric material 220, away from the central region 221. The substrate 230 does not interfere with vision because it is too close to the eye to be in focus and is positioned away from the central region 221 where incident light is transmitted to the eye-sensing portions of the eye. Moreover, the substrate 230 can be formed of a transparent material to further mitigate effects on visual perception.

The substrate 230 can be shaped as a flat, circular ring (e.g., a disk with a centered hole). The flat surface of the substrate 230 (e.g., along the radial width) is a platform for mounting electronics such as chips (e.g., via flip-chip mounting) and for patterning conductive materials (e.g., via microfabrication techniques such as photolithography, deposition, plating, etc.) to form electrodes, antenna(e), and/or interconnections. The substrate 230 and the polymeric material 220 can be approximately cylindrically symmetric about a common central axis. The substrate 230 can have, for example, a diameter of about 10 millimeters, a radial width of about 1 millimeter (e.g., an outer radius 1 millimeter greater than an inner radius), and a thickness of about 50 micrometers. However, these dimensions are provided for example purposes only, and in no way limit the present disclosure. The substrate 230 can be implemented in a variety of different form factors, similar to the discussion of the substrate 130 in connection with FIG. 1 above.

A loop antenna 270, controller 250, and bio-interactive electronics 260 are disposed on the embedded substrate 230. The controller 250 can be a chip including logic elements configured to operate the bio-interactive electronics 260 and the loop antenna 270. The controller 250 is electrically connected to the loop antenna 270 by interconnects 257 also situated on the substrate 230. Similarly, the controller 250 is electrically connected to the bio-interactive electronics 260 by an interconnect 251. The interconnects 251, 257, the loop antenna 270, and any conductive electrodes (e.g., for an electrochemical analyte bio-sensor, etc.) can be formed from conductive materials patterned on the substrate 230 by a process for precisely patterning such materials, such as deposition, photolithography, etc. The conductive materials patterned on the substrate 230 can be, for example, gold, platinum, palladium, titanium, carbon, aluminum, copper, silver, silver-chloride, conductors formed from noble materials, metals, combinations of these, etc.

As shown in FIG. 2A, which is a view facing the concave surface 226 of the eye-mountable device 210, the bio-interactive electronics module 260 is mounted to a side of the substrate 230 facing the concave surface 226. Where the bio-interactive electronics module 260 includes an analyte bio-sensor, for example, mounting such a bio-sensor on the substrate 230 to be close to the concave surface 226 allows the bio-sensor to sense analyte concentrations in tear film near the surface of the eye. However, the electronics, electrodes, etc. situated on the substrate 230 can be mounted to either the "inward" facing side (e.g., situated closest to the concave surface 226) or the "outward" facing side (e.g., situated closest to the convex surface 224). Moreover, in some embodiments, some electronic components can be mounted on one side of the substrate 230, while other electronic components are mounted to the opposing side, and connections between the two can be made through conductive materials passing through the substrate 230.

The loop antenna 270 is a layer of conductive material patterned along the flat surface of the substrate to form a flat conductive ring. In some instances, the loop antenna 270 can be formed without making a complete loop. For instances, the antenna 270 can have a cutout to allow room for the controller 250 and bio-interactive electronics 260, as illustrated in FIG. 2A. However, the loop antenna 270 can also be arranged as a continuous strip of conductive material that wraps entirely around the flat surface of the substrate 230 one or more times. For example, a strip of conductive material with multiple windings can be patterned on the side of the substrate 230 opposite the controller 250 and bio-interactive electronics 260. Interconnects between the ends of such a wound antenna (e.g., the antenna leads) can then be passed through the substrate 230 to the controller 250.

Figure 2D:
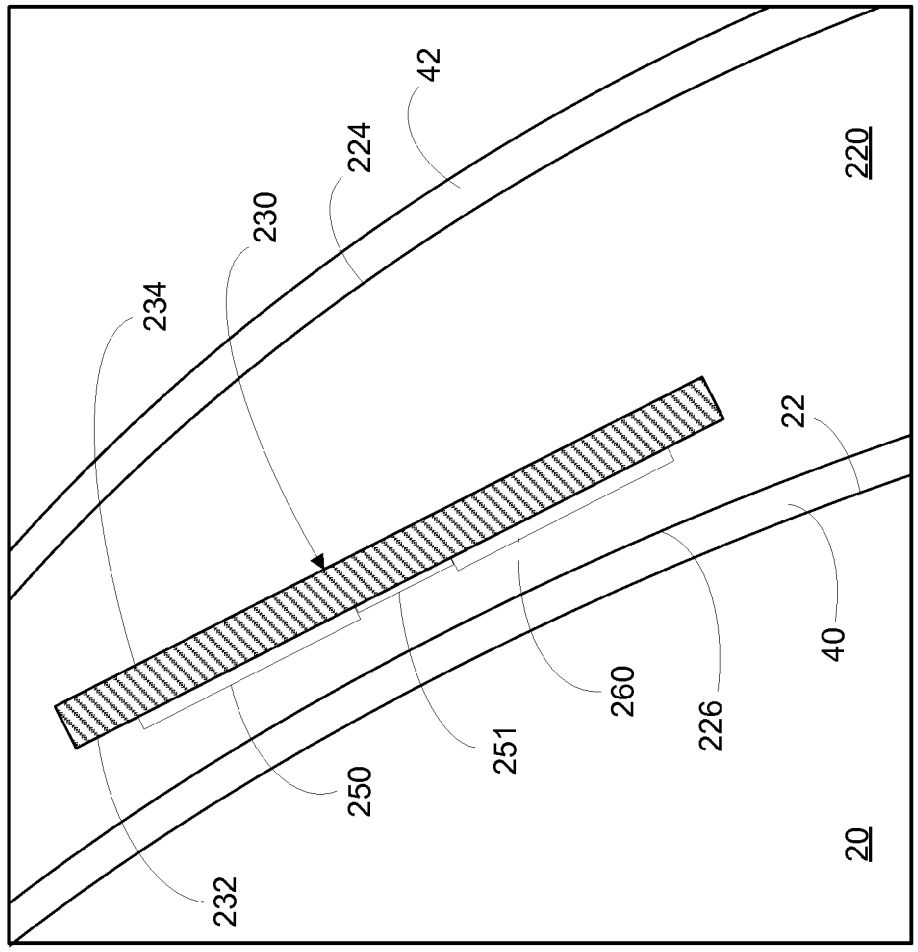
FIG. 2D is a side cross-section view enhanced to show the tear film layers surrounding the surfaces of the example eye-mountable device when mounted as shown in FIG. 2C, in accordance with one embodiment.
Figure 2C:
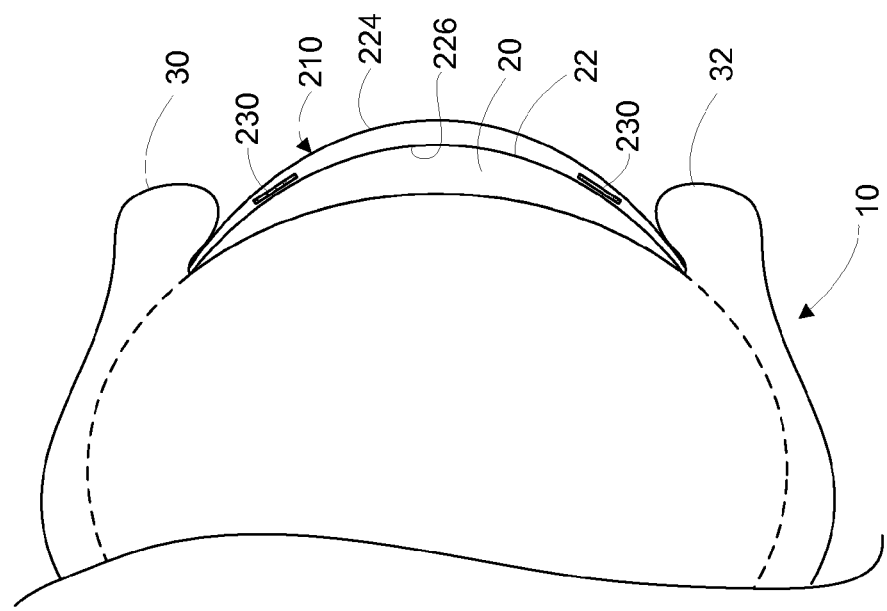
FIG. 2C is a side cross-section view of the example eye-mountable device shown in FIGS. 2A and 2B while mounted to a corneal surface of an eye, in accordance with one embodiment.

FIG. 2C is a side cross-section view of the example eye-mountable electronic device 210 while mounted to a corneal surface 22 of an eye 10. FIG. 2D is a close-in side cross-section view enhanced to show the tear film layers 40, 42 surrounding the exposed surfaces 224, 226 of the example eye-mountable device 210. It is noted that relative dimensions in FIGS. 2C and 2D are not necessarily to scale, but have been rendered for purposes of explanation only in describing the arrangement of the example eye-mountable electronic device 210. For example, the total thickness of the eye-mountable device can be about 200 micrometers, while the thickness of the tear film layers 40, 42 can each be about 10 micrometers, although this ratio may not be reflected in the figures. Some aspects are exaggerated to allow for illustration and facilitate explanation.

The eye 10 includes a cornea 20 that is covered by bringing the upper eyelid 30 and lower eyelid 32 together over the top of the eye 10. Incident light is received by the eye 10 through the cornea 20, where light is optically directed to light sensing elements of the eye 10 (e.g., rods and cones, etc.) to stimulate visual perception. The motion of the eyelids 30, 32 distributes a tear film across the exposed corneal surface 22 of the eye 10. The tear film is an aqueous solution secreted by the lacrimal gland to protect and lubricate the eye 10. When the eye-mountable device 210 is mounted in the eye 10, the tear film coats both the concave and convex surfaces 224, 226 with an inner layer 40 (along the concave surface 226) and an outer layer 42 (along the convex layer 224). The tear film layers 40, 42 can be about 10 micrometers in thickness and together account for about 10 microliters.

The tear film layers 40, 42 are distributed across the corneal surface 22 and/or the convex surface 224 by motion of the eyelids 30, 32. For example, the eyelids 30, 32 raise and lower, respectively, to spread a small volume of tear film across the corneal surface 22 and/or the convex surface 224 of the eye-mountable device 210. The tear film layer 40 on the corneal surface 22 also facilitates mounting the eye-mountable device 210 by capillary forces between the concave surface 226 and the corneal surface 22. In some embodiments, the eye-mountable device 210 can also be held over the eye in part by vacuum forces against corneal surface 22 due to the concave curvature of the eye-facing concave surface 226.

As shown in the cross-sectional views in FIGS. 2C and 2D, the substrate 230 can be inclined such that the flat mounting surfaces of the substrate 230 are approximately parallel to the adjacent portion of the concave surface 226. As described above, the substrate 230 is a flattened ring with an inward-facing surface 232 (closer to the concave surface 226 of the polymeric material 220) and an outward-facing surface 234 (closer to the convex surface 224). The substrate 230 can have electronic components and/or patterned conductive materials mounted to either or both mounting surfaces 232, 234. As shown in FIG. 2D, the bio-interactive electronics 260, controller 250, and conductive interconnect 251 are mounted on the inward-facing surface 232 such that the bio-interactive electronics 260 are relatively closer in proximity to the corneal surface 22 than if they were mounted on the outward-facing surface 234.

III. Example Ophthalmic Electrochemical Analyte Sensor

Figure 3:
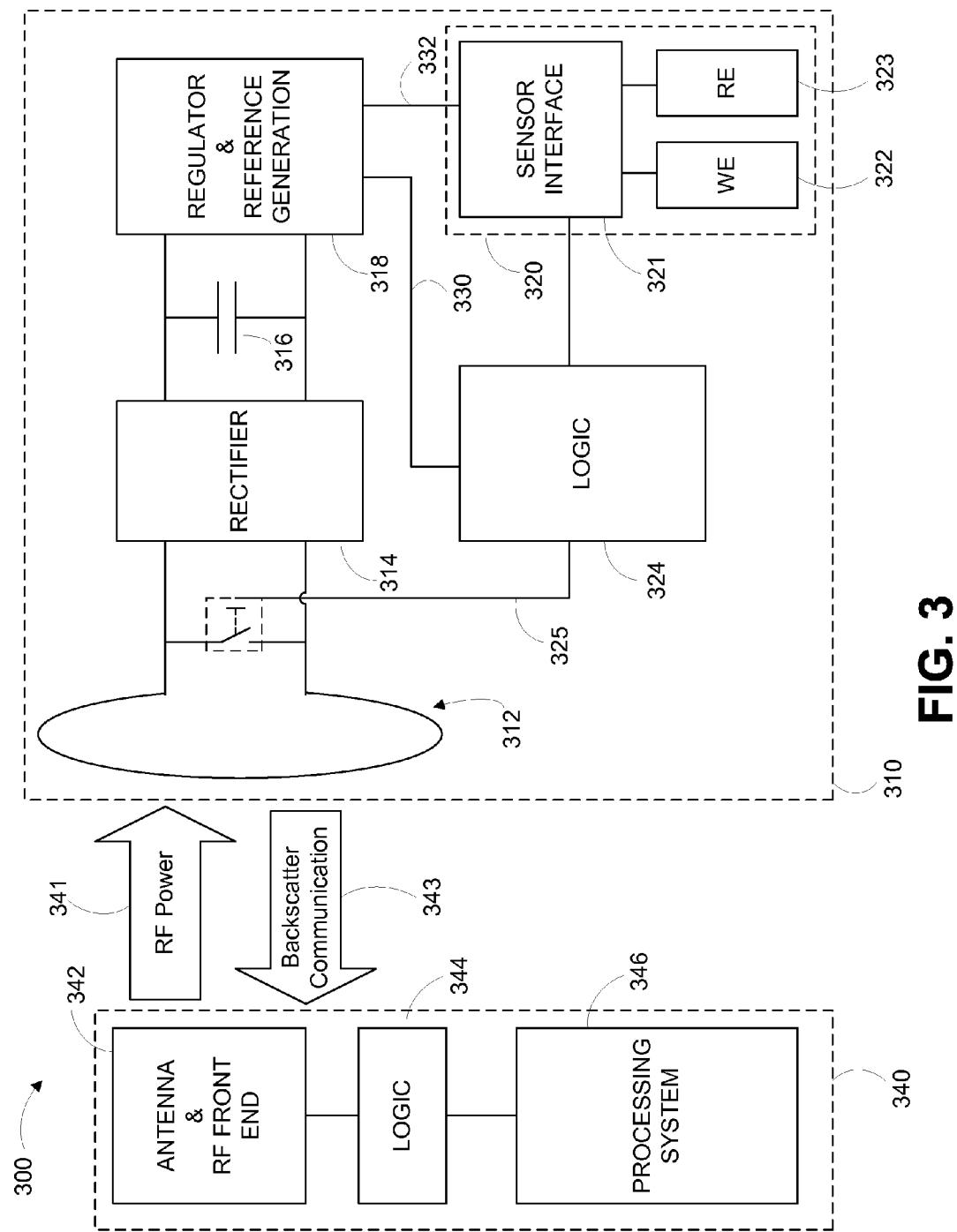
FIG. 3 is a functional block diagram of an example system for electrochemically measuring a tear film analyte concentration, in accordance with one embodiment.

FIG. 3 is a functional block diagram of a system 300 for electrochemically measuring a tear film analyte concentration. As a general matter, the tear film is an aqueous layer secreted from the lacrimal gland to coat the eye. The tear film is in contact with the blood supply through capillaries in the structure of the eye and includes many biomarkers found in blood that are analyzed to characterize a person's health condition(s). For example, the tear film includes glucose, calcium, sodium, cholesterol, potassium, other biomarkers, etc. The biomarker concentrations in the tear film can be systematically different than the corresponding concentrations of the biomarkers in the blood, but a relationship between the two concentration levels can be established to map tear film biomarker concentration values to blood concentration levels. For example, the tear film concentration of glucose can be established (e.g., empirically determined) to be approximately one tenth the corresponding blood glucose concentration. Although another ratio relationship and/or a non-ratio relationship may be used. Thus, measuring tear film analyte concentration levels provides a non-invasive technique for monitoring biomarker levels in comparison to blood sampling techniques performed by lancing a volume of blood to be analyzed outside a person's body. Moreover, the ophthalmic analyte bio-sensor platform disclosed here can be operated substantially continuously to enable real time monitoring of analyte concentrations.

The system 300 depicts a select set of components in order to illustrate certain functionality. It should be understood that system 300 can include other components not depicted here. As depicted, system 300 includes an eye-mountable device 310 with embedded electronic components powered by an external reader 340. The eye-mountable device 310 includes an antenna 312 for capturing radio frequency radiation 341 from the external reader 340. The eye-mountable device 310 includes a rectifier 314, an energy storage 316, and regulator 318 for generating power supply voltages 330, 332 to operate the embedded electronics. The eye-mountable device 310 includes an electrochemical sensor 320 with a working electrode 322 and a reference electrode 323 driven by a sensor interface 321. The eye-mountable device 310 includes hardware logic 324 for communicating results from the sensor 320 to the external reader 340 by modulating the impedance of the antenna 312. An impedance modulator 325 (shown symbolically as a switch in FIG. 3) can be used to modulate the antenna impedance according to instructions from the hardware logic 324. Similar to the eye-mountable devices 110, 210 discussed above in connection with FIGS. 1 and 2, the eye-mountable device 310 can include a mounting substrate embedded within a polymeric material configured to be mounted to an eye.

The electrochemical sensor 320 can be situated on a mounting surface of such a substrate proximate the surface of the eye (e.g., corresponding to the bio-interactive electronics 260 on the inward-facing side 232 of the substrate 230) to measure analyte concentration in a tear film layer interposed between the eye-mountable device 310 and the eye (e.g., the inner tear film layer 40 between the eye-mountable device 210 and the corneal surface 22). In some embodiments, however, an electrochemical sensor can be situated on a mounting surface of such a substrate distal the surface of the eye (e.g., corresponding to the outward-facing side 234 of the substrate 230) to measure analyte concentration in a tear film layer coating the exposed surface of the eye-mountable device 310 (e.g., the outer tear film layer 42 interposed between the convex surface 224 of the polymeric material 210 and the atmosphere and/or closed eyelids).

With reference to FIG. 3, the electrochemical sensor 320 measures analyte concentration by applying a voltage between the electrodes 322, 323 that is sufficient to cause products of the analyte catalyzed by the reagent to electrochemically react (e.g., a reduction and/or oxidization reaction) at the working electrode 322. The electrochemical reactions at the working electrode 322 generate an amperometric current that can be measured at the working electrode 322. The sensor interface 321 can, for example, apply a reduction voltage between the working electrode 322 and the reference electrode 323 to reduce products from the reagent-catalyzed analyte at the working electrode 322. Additionally or alternatively, the sensor interface 321 can apply an oxidization voltage between the working electrode 322 and the reference electrode 323 to oxidize the products from the reagent-catalyzed analyte at the working electrode 322. The sensor interface 321 measures the amperometric current and provides an output to the hardware logic 324. The sensor interface 321 can include, for example, a potentiostat connected to both electrodes 322, 323 to simultaneously apply a voltage between the working electrode 322 and the reference electrode 323 and measure the resulting amperometric current through the working electrode 322.

The rectifier 314, energy storage 316, and voltage regulator 318 operate to harvest energy from received radio frequency radiation 341. The radio frequency radiation 341 causes radio frequency electrical signals on leads of the antenna 312. The rectifier 314 is connected to the antenna leads and converts the radio frequency electrical signals to a DC voltage. The energy storage 316 (e.g., capacitor) is connected across the output of the rectifier 314 to filter out high frequency components of the DC voltage. The regulator 318 receives the filtered DC voltage and outputs both a digital supply voltage 330 to operate the hardware logic 324 and an analog supply voltage 332 to operate the electrochemical sensor 320. For example, the analog supply voltage can be a voltage used by the sensor interface 321 to apply a voltage between the sensor electrodes 322, 323 to generate an amperometric current. The digital supply voltage 330 can be a voltage suitable for driving digital logic circuitry, such as approximately 1.2 volts, approximately 3 volts, etc. Reception of the radio frequency radiation 341 from the external reader 340 (or another source, such as ambient radiation, etc.) causes the supply voltages 330, 332 to be supplied to the sensor 320 and hardware logic 324. While powered, the sensor 320 and hardware logic 324 are configured to generate and measure an amperometric current and communicate the results.

The sensor results can be communicated back to the external reader 340 via backscatter radiation 343 from the antenna 312. The hardware logic 324 receives the output current from the electrochemical sensor 320 and modulates (325) the impedance of the antenna 312 in accordance with the amperometric current measured by the sensor 320. The antenna impedance and/or change in antenna impedance is detected by the external reader 340 via the backscatter signal 343. The external reader 340 can include an antenna front end 342 and logic components 344 to decode the information indicated by the backscatter signal 343 and provide digital inputs to a processing system 346. The external reader 340 associates the backscatter signal 343 with the sensor result (e.g., via the processing system 346 according to a pre-programmed relationship associating impedance of the antenna 312 with output from the sensor 320). The processing system 346 can then store the indicated sensor results (e.g., tear film analyte concentration values) in a local memory and/or an external memory (e.g., by communicating with the external memory through a network).

In some embodiments, one or more of the features shown as separate functional blocks can be implemented ("packaged") on a single chip. For example, the eye-mountable device 310 can be implemented with the rectifier 314, energy storage 316, voltage regulator 318, sensor interface 321, and the hardware logic 324 packaged together in a single chip or controller module. Such a controller can have interconnects ("leads") connected to the loop antenna 312 and the sensor electrodes 322, 323. Such a controller operates to harvest energy received at the loop antenna 312, apply a voltage between the electrodes 322, 323 sufficient to develop an amperometric current, measure the amperometric current, and indicate the measured current via the antenna 312 (e.g., through the backscatter radiation 343).

Whereas the device described herein is described as comprising the eye-mountable device 110 and/or the eye-mountable device 310, the device could comprise other devices that are mounted on or in other portions of the human body.

For example, in some embodiments, the body-mountable device may comprise a tooth-mountable device. In some embodiments, the tooth-mountable device may take the form of or be similar in form to the eye-mountable device 110 and/or the eye-mountable device 310. For instance, the tooth-mountable device could include a polymeric material or a transparent polymer that is the same or similar to any of the polymeric materials or transparent polymers described herein and a substrate or a structure that is the same or similar to any of the substrates or structures described herein. With such an arrangement, the tooth-mountable device may be configured to detect at least one analyte in a fluid (e.g., saliva) of a user wearing the tooth-mountable device.

Moreover, in some embodiments, the body-mountable device may comprise a skin-mountable device. In some embodiments, the skin-mountable device may take the form of or be similar in form to the eye-mountable device 110 and/or the eye-mountable device 310. For instance, the skin-mountable device could include a polymeric material or a transparent polymer that is the same or similar to any of the polymeric materials or transparent polymers described herein and a substrate or a structure that is the same or similar to any of the substrates or structures described herein. With such an arrangement, the skin-mountable device may be configured to detect at least one analyte in a fluid (e.g., perspiration, blood, etc.) of a user wearing the skin-mountable device.

Figure 4A:
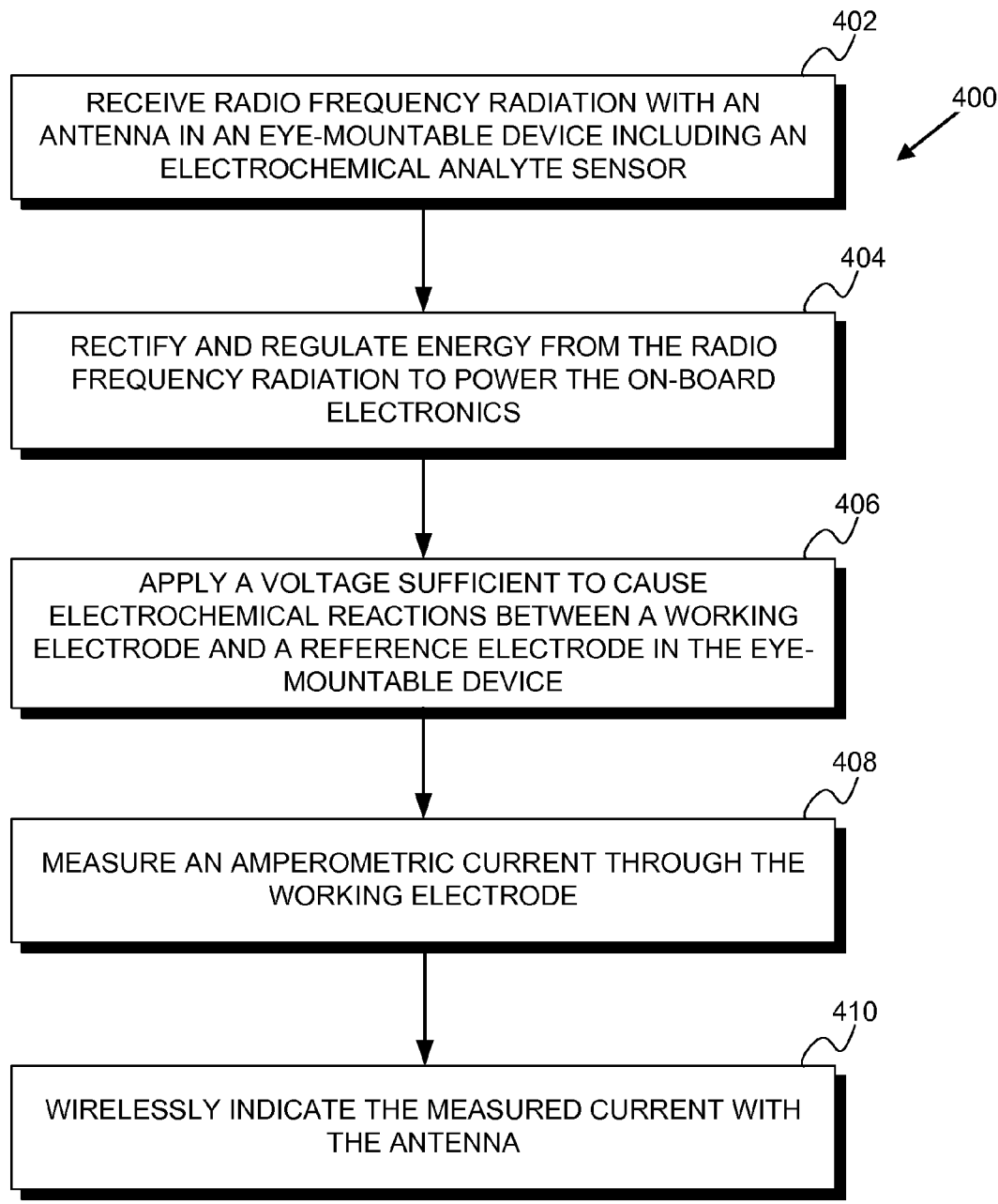
FIG. 4A is a flowchart of an example process for operating an amperometric sensor in an eye-mountable device to measure a tear film analyte concentration, in accordance with one embodiment.

FIG. 4A is a flowchart of a process 400 for operating an amperometric sensor in an eye-mountable device to measure a tear film analyte concentration. Radio frequency radiation is received at an antenna in an eye-mountable device including an embedded electrochemical sensor (402). Electrical signals due to the received radiation are rectified and regulated to power the electrochemical sensor and associated controller (404). For example, a rectifier and/or regulator can be connected to the antenna leads to output a DC supply voltage for powering the electrochemical sensor and/or controller. A voltage sufficient to cause electrochemical reactions at the working electrode is applied between a working electrode and a reference electrode on the electrochemical sensor (406). An amperometric current is measured through the working electrode (408). For example, a potentiostat can apply a voltage between the working and reference electrodes while measuring the resulting amperometric current through the working electrode. The measured amperometric current is wirelessly indicated with the antenna (410). For example, backscatter radiation can be manipulated to indicate the sensor result by modulating the antenna impedance.

Figure 4B:
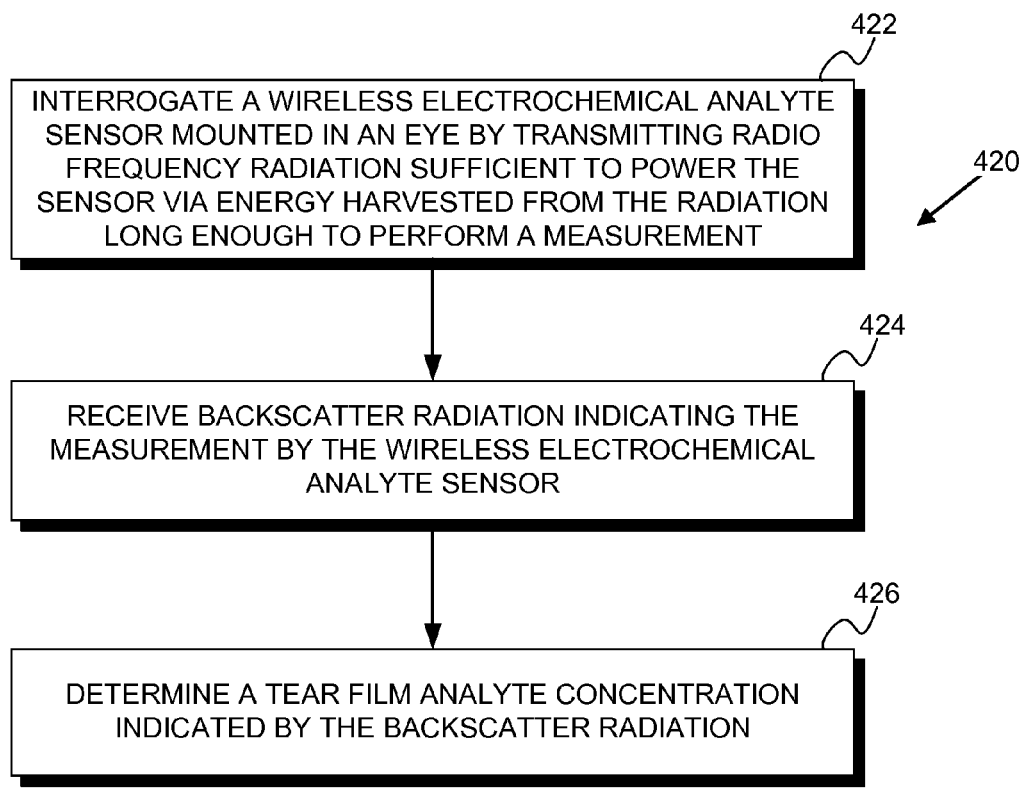
FIG. 4B is a flowchart of an example process for operating an external reader to interrogate an amperometric sensor in an eye-mountable device to measure a tear film analyte concentration, in accordance with one embodiment.

FIG. 4B is a flowchart of a process 420 for operating an external reader to interrogate an amperometric sensor in an eye-mountable device to measure a tear film analyte concentration. Radio frequency radiation is transmitted to an electrochemical sensor mounted in an eye from the external reader (422). The transmitted radiation is sufficient to power the electrochemical sensor with energy from the radiation for long enough to perform a measurement and communicate the results (422). For example, the radio frequency radiation used to power the electrochemical sensor can be similar to the radiation 341 transmitted from the external reader 340 to the eye-mountable device 310 described in connection with FIG. 3 above. The external reader then receives backscatter radiation indicating the measurement by the electrochemical analyte sensor (424). For example, the backscatter radiation can be similar to the backscatter signals 343 sent from the eye-mountable device 310 to the external reader 340 described in connection with FIG. 3 above. The backscatter radiation received at the external reader is then associated with a tear film analyte concentration (426). In some cases, the analyte concentration values can be stored in the external reader memory (e.g., in the processing system 346) and/or a network-connected data storage.

For example, the sensor result (e.g., the measured amperometric current) can be encoded in the backscatter radiation by modulating the impedance of the backscattering antenna. The external reader can detect the antenna impedance and/or change in antenna impedance based on a frequency, amplitude, and/or phase shift in the backscatter radiation. The sensor result can then be extracted by associating the impedance value with the sensor result by reversing the encoding routine employed within the eye-mountable device. Thus, the reader can map a detected antenna impedance value to an amperometric current value. The amperometric current value is approximately proportionate to the tear film analyte concentration with a sensitivity (e.g., scaling factor) relating the amperometric current and the associated tear film analyte concentration. The sensitivity value can be determined in part according to empirically derived calibration factors, for example.

IV. Example Electrochemical Sensor With Dual Power Sources

FIG. 5A is a functional block diagram of an example electrochemical sensor system 500 including a measurement power supply 510 and an auxiliary power supply 520. The electrochemical sensor system 500 can also include a working electrode 502, a reference electrode 504, an antenna 522, measurement and communication electronics 524, photocell 526 and auxiliary electronics 528. Although, it is noted the functional block diagram of the system 500 shown in FIG. 5A illustrates separate functional modules, they are not necessarily implemented as physically distinct modules. For example, the measurement power supply 510 and measurement and communication electronics 524 can be packaged in a common chip that includes terminals connected to the antenna 522 and the sensor electrodes 502, 504. Further, while not specifically illustrated, it is noted that a reagent layer can be provided on or near the working electrode 502 to sensitize the electrochemical sensor to an analyte of interest. For example, glucose oxidase may be fixed around the working electrode 502 (e.g., by incorporating glucose oxidase in a gel or medium) to cause the electrochemical sensor system 500 to detect glucose.

As shown, measurement power supply 510 and auxiliary power supply 520 are electrically connected to the measurement and control electronics 524 in order to supply power (e.g., a DC supply voltage) to the system 500. For brevity, the measurement and control electronics 524 is alternately referred to herein as the "measurement electronics" or the "measurement module." Generally, the measurement and control electronics 524, which receive power from the measurement power supply 510 and/or the auxiliary power supply 520, may apply a voltage across the sensor electrodes 502, 504 while obtaining an amperometric current measurement (e.g., similar to the operation of a potentiostat).

In accordance with one embodiment, the measurement power supply 510 depicted in FIG. 5A operates to harvest energy from incident radio frequency radiation and generate a DC supply voltage to turn on the measurement and communication electronics 524, thereby causing the system 500 to obtain an amperometric current measurement through the working electrode 502 and communicate the sensor result through antenna 522. The measurement power supply 510 may be a power supply that is dedicated to providing power to the measurement and control electronics 524. The measurement power supply 510 can generally be similar to the energy harvesting power supply system described in connection with FIGS. 1 and 3 and may include one or more rectifiers, energy storage devices, and/or voltage regulators/conditioners configured to harvest energy in radio frequency electrical signals on leads of the antenna 522 caused by incident radiation and output a DC supply voltage to power the measurement and communication electronics 524.

In accordance with one embodiment, the auxiliary power supply 520 depicted in FIG. 5A operates to harvest energy other than that received from the from the radio frequency energy harvesting antenna 522. For example, in some embodiments, the auxiliary power supply 520 may comprise a photovoltaic cell (e.g., the photovoltaic cell 526) that outputs a voltage across two terminals in response to incident light radiation. The terminals of the photovoltaic cell 526 can then be connected to the measurement and communication electronics 524, so that voltage output from the photovoltaic cell 526 can turn on the measurement and communication electronics 524, thereby causing the system 500 to obtain an amperometric current measurement through the working electrode 502.

The photovoltaic cell 526 can be, for example, a solar cell or a combination of such solar cells. The photovoltaic cell can be activated in response to the receipt of light at a range of different wavelengths, such as visible light, ultraviolet light, near infrared light, etc. Although, a particular photovoltaic cell may be configured to be activated at a selected range of wavelengths as desired. In an embodiment in which the electrochemical sensor is included in an eye-mountable device (e.g., embedded in a transparent polymeric material configured to be contact-mounted to an eye surface) the photovoltaic cell 526 can be embedded in the eye-mountable device and can receive incident light radiation that is transmitted through the eye-mountable device.

In other embodiments, however, the auxiliary power supply 520 is additionally or alternatively powered via another energy harvesting source, such as an inertial motion energy harvesting system, a biofuel cell, and/or a charge storage device. The biofuel cell may be configured to facilitate a chemical reaction and generate a responsive electric potential. In one example, the biofuel cell facilitates oxidation of the ascorbate naturally present in tear fluid. However, other types of bio fuel cells are possible as well. Still additionally, the auxiliary power supply may comprise a charge storage device, such as a rechargeable battery or an arrangement of capacitors. The charge storage device may be arranged to store electric charge generated by the photovoltaic cell, inertial motion energy harvesting system, biofuel cell, antenna, or other charge generating device.

In some embodiments, the measurement power supply 510 and the auxiliary power supply 520 include components similar to the voltage regulator and/or rectifier 314, 318 described in connection with FIG. 3 that outputs both an analog voltage 332 to the sensor interface 321, and a DC supply voltage 330 to the circuit logic 324. With reference to the system 500 in FIG. 5A, the voltage applied across the sensor electrodes 502, 504 may be analogous to the analog voltage output of the energy harvesting system, while the DC supply voltage provided to the measurement and communication electronics 524 can be analogous to the digital voltage output of the energy harvesting system. Thus, some embodiments of the measurement power supply 510 and auxiliary power supply 520 may include a rectifier, a low-pass filter (e.g., one or more capacitors), and/or voltage regulation/conditioning modules that may be similar in some respects to the rectifier 314, energy storage 316, and/or voltage regulator/conditioner 318 described in connection with FIG. 3 above.

The measurement and communication electronics 524 are shown and described in connection with FIG. 5A as a functional module that receives a DC supply voltage, obtains an amperometric current measurement measured through the working electrode, and then operates the antenna 522 to communicate the measured current. However, the measurement and communication electronics may include one or more of the functional modules shown and described in connection with FIG. 3 above, such as a sensor interface (e.g., a potentiostat), an antenna interface (e.g., a backscatter radiation modulator, one or more oscillators, etc.), and/or logic elements configured to cause the module 524 to function as described. Moreover, while the measurement and communication electronics are shown and described as a single physical module, it is noted that the measurement and communication electronics 524 can include a combination of one or more modules, or can be combined with other modules (e.g., rectifier, regulator and/or other related power supply modules) in a single physical implementation, such as an integrated circuit or chip.

In accordance with some embodiments, system 500 also includes auxiliary electronics 528. Auxiliary electronics 528 are shown and described in connection with FIG. 5A as a functional module that receives a DC supply voltage from auxiliary power supply 520. The auxiliary electronics 528 may include one or more of the functional modules shown and described in connection with FIG. 1 above, such a pixel array, radio transceiver, memory storage, and/or logic elements configured to cause the auxiliary electronics 528 to function as described. Moreover, while auxiliary electronics 528 are shown as a single physical module, it is noted that the auxiliary electronics 528 can include a combination of one or more modules, or can be combined with other modules (e.g., rectifier, regulator and/or other related power supply modules) in a single physical implementation, such as an integrated circuit or chip.

In operation according to some embodiments, system 500 may contain an appropriate mechanism that operates to determine when the auxiliary power supply 520 is able to provide power to the system 500 and responsively enable the auxiliary power supply 520. For example, in embodiments in which the auxiliary power supply is powered by a photovoltaic cell 526, auxiliary power supply 520 may contain an ambient light detector that operates to detect the presence of ambient light sufficient enough for the photovoltaic cell 526 to provide an operating voltage (e.g., 5.0V) to the measurement and communication electronics 524 and/or the auxiliary electronics 528. In embodiments in which the auxiliary power supply is powered by a biofuel cell, auxiliary power supply 520 may recognize when the biofuel cell is producing a voltage level (e.g., 5.0V) that is sufficient enough to operate the measurement and communication electronics 524 and/or the auxiliary electronics 528. In embodiments in which the auxiliary power supply is powered by a charge storage device, auxiliary power supply 520 may determine whether the charge storage device has stored a sufficient level of electric charge (e.g., 5.0V) to operate the measurement and communication electronics 524 and/or the auxiliary electronics 528. In embodiments in which the auxiliary power supply 520 is powered by an inertial motion energy harvesting system, the auxiliary power supply 520 may contain a motion detector that operates to determine when there is motion sufficient enough for the motion detector to provide an operating voltage (e.g., 5.0V) to the measurement and communication electronics 524 and/or the auxiliary electronics 528. However, in other embodiments, other mechanisms for determining whether the auxiliary power supply 520 is able to provide power to the system 500 are possible as well.

As mentioned above, in response to determining that the auxiliary power supply 520 is able to provide sufficient power to the communication electronics 524 and/or the auxiliary electronics 528, the auxiliary power supply 520 may operate to enable the auxiliary power supply 520. In some embodiments, this is carried out by providing to a switch or other logic a signal indicative of the availability of the auxiliary power supply 520 to provide power to the system 500. The switch or other logic may responsively enable and operate the auxiliary power supply 520 to provide power to the measurement and communication electronics 524 and/or the auxiliary electronics 528 (e.g., by closing a circuit, thereby electrically coupling the auxiliary power supply to either or both of the measurement and communication electronics 524 and the auxiliary electronics 528). However, other ways of enabling the auxiliary power supply 520 are possible as well.

In practice, opportunistic enabling of auxiliary power supply 520 may have several operational advantages. For instance, in a situation in which the auxiliary electronics 528 are being powered by measurement power supply 510, enabling auxiliary power supply 520 may result in additional power being supplied to the auxiliary electronics 528 from the auxiliary power supply 520. As such, the additional power may result in an improved performance of one or more of the auxiliary electronics. For example, when the auxiliary electronics 528 include a Bluetooth radio, providing additional power to the radio may enable the radio to transmit a farther distance. Other examples of improved performance are possible as well.

In another example of an operational advantage, enabling auxiliary power supply 520 to provide power to the system 500 may allow the measurement power supply 510 to reduce the amount of power it supplies to the system 500. As such, while the auxiliary power supply 520 powers the system 500, power may be preserved at the measurement power supply 510 and/or an external reader associated with the measurement power supply 510. In some embodiments, the auxiliary power supply 520 in conjunction with the measurement and communication electronics 524 include logic configured for determining whether the auxiliary power supply 520 is supplying power to the system 500 and responsively causing the measurement power supply 510 to reduce the amount of power supplied to the system 500. In one example of this, the measurement and communication electronics 524 operate to characteristically modify RF backscatter at antenna 526 to communicate with an external reader. Accordingly, this communication may cause the external reader to temporarily reduce or stop the external reader's transmission of power to the measurement power supply 510. However, other ways of conserving power are possible as well.

In another example of an operational advantage, enabling auxiliary power supply 520 to provide power to auxiliary electronics 528 may allow system 500 to retain an operating state during periods in which the measurement power supply 510 is unable to provide power to the system 500. For instance, when auxiliary electronics 528 include a volatile memory storage unit (i.e., a memory storage unit that loses its contents when power is removed from the memory storage unit) that stores certain operating parameters (e.g., measurement results), those parameters may be lost when power is removed from the volatile memory storage unit. Therefore, when the auxiliary power supply 520 provides power to the volatile memory storage unit, the operating parameters contained therein may not be lost when the measurement power supply 510 stops providing power to system 500. In addition, in some embodiments, system 500 may contain logic configured for determining that the measurement power supply is (or will soon be) unable to provide power but the auxiliary power supply is able to provide power. In response to this determination, the system 500 may enable the auxiliary power supply 520 to provide power to the volatile memory storage unit. In one example, the system 500 determines that the measurement power supply 510 is (or will soon be) unable to provide power by receiving an instruction (e.g., in the form of RF radiation received at antenna 522 from an external reader) that indicates that the external reader is powering down. However, other ways of determining that the measurement power supply 510 is (or will soon be) unable to provide power are possible as well.

In operation according to additional or alternative embodiments, system 500 may contain logic configured for determining an intention to operate auxiliary electronics 528 and responsively enabling and operating the auxiliary power supply 520 to provide power to the auxiliary power electronics 528. For instance, system 500 may receive an instruction (e.g., in the form of RF radiation received at antenna 522 from an external reader) that instructs system 500 to operate at least part of auxiliary electronics 528, such as pixel array 164. In response, auxiliary power supply 520 may provide to a switch or other logic a signal indicative of an intent to operate the auxiliary electronics 528. The switch or other logic may responsively enable and operate the auxiliary power supply 520 to provide power to the auxiliary electronics 528 (e.g., by closing a circuit, thereby electrically coupling the auxiliary power supply to the auxiliary electronics 528). In this way, auxiliary electronics embedded within the eye-mountable device, such as a Bluetooth radio or a pixel array, can be opportunistically operated when there is sufficient power able to be harvested from sources other than the external reader, thereby conserving battery life of the external reader.

In operation according to additional or alternative embodiments, system 500 may contain logic configured for determining that the auxiliary power supply is unable to currently supply power and responsively entering a lower power mode in which the system 500 disables all auxiliary electronics but for the sensor 501. Entering a low power mode, such as this one, may help the system 500 generally, and the measurement power supply 510 (as well as an associated external reader) in particular, conserve power. Depending on the embodiment, the system 500 may determine that the auxiliary power supply 520 is unable to supply power by detecting that there is insufficient light for the photovoltaic cell 526 to provide an operating voltage (e.g., 5.0V) to the measurement and communication electronics 524 and/or the auxiliary electronics 528, the biofuel cell is not producing a voltage level (e.g., 5.0V) that is sufficient enough to operate the measurement and communication electronics 524 and/or the auxiliary electronics 528, the charge storage device has stored an insufficient level of electric charge (e.g., <5.0V) to operate the measurement and communication electronics 524 and/or the auxiliary electronics 528, there is not sufficient enough motion for the motion detector to provide an operating voltage (e.g., 5.0V) to the measurement and communication electronics 524 and/or the auxiliary electronics 528, or in other ways as well.

FIG. 5B is a flowchart of an example process 530 for operating the example electrochemical sensor system 500 of FIG. 5A. The example process 530 may include one or more operations, functions, or actions, as depicted by one or more of blocks 532, 534, and/or 536, each of which may be carried out by any of the systems described herein; however, other configurations could be used.

Furthermore, those skilled in the art will understand that flow diagrams described herein illustrate functionality and operation of certain implementations of example embodiments. In this regard, each block of each flow diagram may represent a module, a segment, or a portion of program code, which includes one or more instructions executable by a processor (e.g., a processor of controller 150 described above with respect to FIG. 1) for implementing specific logical functions or steps in the process. The program code may be stored on any type of computer readable medium (e.g., computer readable storage medium or non-transitory media), for example, such as a storage device including a disk or hard drive. In addition, each block may represent circuitry that is wired to perform the specific logical functions in the process. Alternative implementations are included within the scope of the example embodiments of the present application in which functions may be executed out of order from that shown or discussed, including substantially concurrent or in reverse order, depending on the functionality involved, as would be understood by those reasonably skilled in the art.

The process 530 begins at block 532 where the system 500 receives a signal indicative of the availability of the auxiliary power supply to supply power to the system 500. As described, in embodiments in which the auxiliary power supply receives power from a photovoltaic cell, such a signal may take the form of the output of an ambient light detector. In one example, the signal comprises a determination that the level of ambient light incident upon the photovoltaic cell is at or above a threshold level of ambient light. Generally, in this example, the threshold level of ambient light is a level at which the photovoltaic cell and the auxiliary power supply can provide a sufficient DC voltage (e.g., 5.0 Volts) to operate the auxiliary electronics and/or the measurement and communication electronics. In embodiments in which the auxiliary power source receives power from another type of energy-harvesting device, the signal may be one that is generally indicative of that device's ability to imminently provide a DC power supply to the auxiliary electronics and/or the measurement and communication electronics sufficient to power such electronics.

The process continues at block 534, where the system 500 enables the auxiliary power supply. As described, in some embodiments, enabling the auxiliary power supply includes a switch or other actuating device that can electrically couple the auxiliary power supply to the auxiliary electronics and/or the measurement and communication electronics upon receipt of the signal described in connection with block 532. And finally, in block 536, the system operates the auxiliary power supply to provide power to the electrochemical sensor. As described, in one embodiment, operating the auxiliary power supply to provide power may include receiving incident light at the photovoltaic cell and converting the light into a DC supply voltage. In another embodiment, operating the auxiliary power supply to provide power may include harvesting motion energy and converting such energy into a DC supply voltage. In other embodiments, other energy harvesting devices are possible and in those embodiments, operating the auxiliary power supply generally includes converting the harvested energy into a DC supply voltage.

FIG. 5C is another flowchart of an example process 540 for operating the example electrochemical sensor system 500 of FIG. 5A. The example process 540 may include one or more operations, functions, or actions, as depicted by one or more of blocks 542, 544, and/or 546, each of which may be carried out by any of the systems described herein; however, other configurations could be used.

The process 540 begins at block 542 where the system 500 receives a signal indicative of an intention to operate an auxiliary device. As described, in embodiments in which the auxiliary electronics include a pixel array, such a signal may take the form of an instruction to operate the pixel array. In some embodiments, this instruction may be generated at a controller of system 500 (e.g., controller 150 described in connection with FIG. 1). Additionally or alternatively, this instruction may be received from an external reader (e.g., external reader 180 described in connection with FIG. 1).

The process continues at block 544, where the system 500 enables the auxiliary power supply. Similar to that described above in connection with block 534 of FIG. 5B, the auxiliary power supply may include a switch or other actuating device that can electrically couple the auxiliary power supply to the auxiliary electronics and/or the measurement and communication electronics upon receipt of the signal described in connection with block 542. And finally, in block 546, similar to that described above in connection with block 536 of FIG. 5B, the system operates the auxiliary power supply to provide power to the auxiliary device. As described, in one embodiment, operating the auxiliary power supply to provide power may include receiving incident light at the photovoltaic cell and converting the light into a DC supply voltage. In another embodiment, operating the auxiliary power supply to provide power may include harvesting motion energy and converting such energy into a DC supply voltage. In other embodiments, other energy harvesting devices are possible and in those embodiments, operating the auxiliary power supply generally includes converting the harvested energy into a DC supply voltage.

Figure 5D:
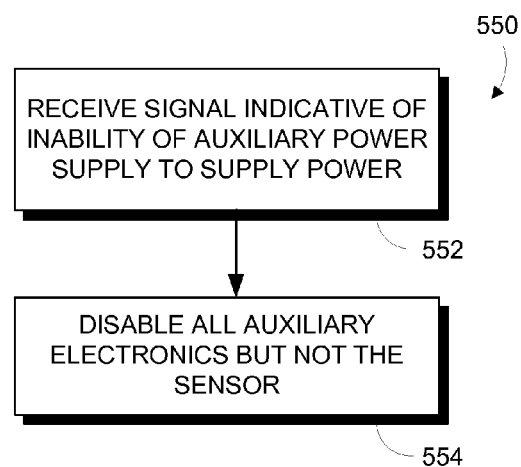
FIG. 5D is a flowchart of an example process for operating the example electrochemical sensor of FIG. 5A, in accordance with one embodiment.

FIG. 5D is a flowchart of an example process 550 for operating the example electrochemical sensor system 500 of FIG. 5A. The example process 550 may include one or more operations, functions, or actions, as depicted by one or more of blocks 552 and/or 554, each of which may be carried out by any of the systems described herein; however, other configurations could be used.

The process 550 begins at block 552 where the system 500 receives a signal indicative of the inability of the auxiliary power supply to supply power to the system 500. As described, in embodiments in which the auxiliary power supply receives power from a photovoltaic cell, such a signal may take the form of the output of an ambient light detector. In one example, the signal comprises a determination that the level of ambient light incident upon the photovoltaic cell is below a threshold level of ambient light. Generally, in this example, the threshold level of ambient light is a level at which the photovoltaic cell and the auxiliary power supply can provide a sufficient DC voltage (e.g., 5.0 Volts) to operate the auxiliary electronics and/or the measurement and communication electronics. In embodiments in which the auxiliary power source receives power from another type of energy-harvesting device, the signal may be one that is generally indicative of that device's inability to imminently provide a DC power supply to the auxiliary electronics and/or the measurement and communication electronics sufficient to power such electronics.

The process continues at block 554, where the system 500 enters a low power mode in which it disables all the auxiliary electronics but for the sensor 501. As described, in some embodiments, entering the low power mode may enable the system 500 generally and the measurement power supply in particular to conserve power by not having to power the auxiliary electronics.

Figure 6:
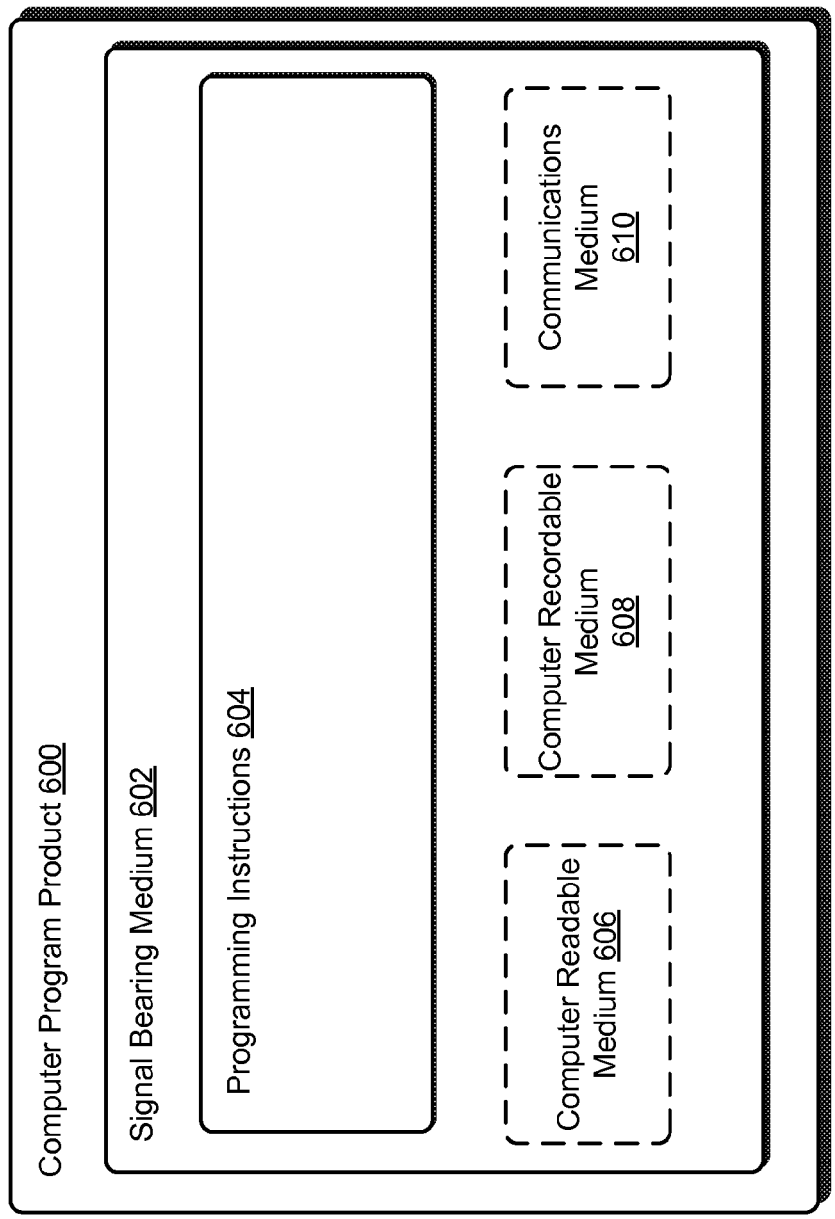
FIG. 6 depicts a computer-readable medium, in accordance with one embodiment.

FIG. 6 depicts a computer-readable medium configured according to an example embodiment. In example embodiments, the example system can include one or more processors, one or more forms of memory, one or more input devices/interfaces, one or more output devices/interfaces, and machine-readable instructions that when executed by the one or more processors cause the system to carry out the various functions, tasks, capabilities, etc., described above.

As noted above, in some embodiments, the disclosed techniques can be implemented by computer program instructions encoded on a non-transitory computer-readable storage media in a machine-readable format, or on other non-transitory media or articles of manufacture (e.g., the instructions 184 stored on the memory storage 182 of the external reader 180 of the system 100). FIG. 6 is a schematic illustrating a conceptual partial view of an example computer program product that includes a computer program for executing a computer process on a computing device, arranged according to at least some embodiments presented herein.

In one embodiment, the example computer program product 600 is provided using a signal bearing medium 602. The signal bearing medium 602 may include one or more programming instructions 604 that, when executed by one or more processors may provide functionality or portions of the functionality described above with respect to FIGS. 1-5C. In some examples, the signal bearing medium 602 can be a non-transitory computer-readable medium 606, such as, but not limited to, a hard disk drive, a Compact Disc (CD), a Digital Video Disk (DVD), a digital tape, memory, etc. In some implementations, the signal bearing medium 602 can be a computer recordable medium 608, such as, but not limited to, memory, read/write (R/W) CDs, R/W DVDs, etc. In some implementations, the signal bearing medium 602 can be a communications medium 610, such as, but not limited to, a digital and/or an analog communication medium (e.g., a fiber optic cable, a waveguide, a wired communications link, a wireless communication link, etc.). Thus, for example, the signal bearing medium 602 can be conveyed by a wireless form of the communications medium 610.

The one or more programming instructions 604 can be, for example, computer executable and/or logic implemented instructions. In some examples, a computing device such as the processor-equipped external reader 180 of FIG. 1 is configured to provide various operations, functions, or actions in response to the programming instructions 604 conveyed to the computing device by one or more of the computer readable medium 606, the computer recordable medium 608, and/or the communications medium 610.

The non-transitory computer readable medium 606 can also be distributed among multiple data storage elements, which could be remotely located from each other. The computing device that executes some or all of the stored instructions could be an external reader, such as the reader 180 illustrated in FIG. 1, or another mobile computing platform, such as a smartphone, tablet device, personal computer, etc. Alternatively, the computing device that executes some or all of the stored instructions could be remotely located computer system, such as a server.

Where example embodiments involve information related to a person or a device of a person, some embodiments may include privacy controls. Such privacy controls may include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

What is claimed is:

1. A method comprising:
at a wearable device that includes at least one sensor, a primary power supply and an auxiliary power supply, receiving a signal indicative of an availability of the auxiliary power supply to provide power to the wearable device; and
responsive to receiving the signal, the wearable device operating the auxiliary power supply to supply power to the wearable device, wherein the primary power supply uses a first type of energy to power the wearable device and the auxiliary power supply uses a second type of energy to power the wearable device, wherein the first type of energy is different from the second type of energy.

2. The method of claim 1,
wherein the primary power supply harvests the first type of energy, and
wherein the auxiliary power supply harvests the second type of energy.

3. The method of claim 2,
wherein the primary power supply harvests radio frequency (RF) radiation received from an external reader and uses the harvested RF radiation to power the at least one sensor, and
wherein the method further comprises responsive to receiving the signal, the wearable device causing the external reader to reduce an amount of RF radiation transmitted to the wearable device.

4. The method of claim 1, wherein the auxiliary power supply comprises a photovoltaic cell, the method further comprising:
based on the received signal, the wearable device determining that there is a threshold level of ambient light incident upon the photovoltaic cell, the threshold level of ambient light causing the photovoltaic cell to produce a voltage level sufficient to operate an auxiliary device associated with the wearable device.

5. The method of claim 1, wherein the auxiliary power supply comprises a battery.

6. The method of claim 1, wherein the at least one sensor includes an electrochemical sensor with a working electrode, a reference electrode, and a reagent that selectively reacts with an analyte.

7. The method of claim 6, wherein the auxiliary power supply comprises a biofuel cell that generates electrical energy in response to a reaction between two catalysts present in tear fluid, the method further comprising:
based on the received signal, the wearable device determining that the biofuel cell is generating a threshold level of electrical energy, the threshold level being sufficient to operate an auxiliary device associated with the wearable device.

8. The method of claim 1, wherein the signal is further indicative of an intention of the wearable device to operate an auxiliary device associated with the wearable device, the auxiliary device including one or more of a radio transmitter, an array of one or more light emitters, and a memory storage device, the method further comprising:
the wearable device operating the auxiliary power supply to supply power to the auxiliary device.

9. The method of claim 1, further comprising:
the wearable device supplying power from the primary power supply to an auxiliary device associated with the wearable device; and
responsive to receiving the signal, the wearable device supplying additional power to the auxiliary device, the auxiliary device thereby receiving power from the primary power supply and the auxiliary power supply.

10. A wearable device comprising:
at least one sensor;
a first power supply that uses a first type of energy;
a second power supply that uses a second type of energy, wherein the first type of energy is different from the second type of energy; and
a controller electrically connected to the first power supply and the second power supply, wherein the controller enables the second power supply in response to a determination that the second power supply is able to supply power.

11. The wearable device of claim 10, further comprising:
auxiliary electronics.

12. The wearable device of claim 11,
wherein the second power supply comprises a photovoltaic cell, and
wherein the determination that the second power supply is able to supply power comprises a determination that there is a threshold level of ambient light incident upon the photovoltaic cell, the threshold level of ambient light causing the photovoltaic cell to produce a voltage level sufficient to operate the auxiliary electronics.

13. The wearable device of claim 11,
wherein the second power supply comprises a charge storage device, and
wherein the determination that the second power supply is able to supply power comprises a determination that there is a threshold level of electric charge stored in the charge storage device, the threshold level of electric charge being sufficient to operate the auxiliary electronics.

14. The wearable device of claim 11,
wherein the second power supply comprises a biofuel cell that generates electrical energy in response to a reaction between two catalysts present in tear fluid, and
wherein the determination that the second power supply is able to supply power comprises a determination that the biofuel cell is generating a threshold level of electrical energy, the threshold level being sufficient to operate the auxiliary electronics.

15. The wearable device of claim 10, further comprising:
a memory storage unit, wherein the controller retains operating parameters in the memory storage unit using the second power supply in response to a determination that the first power supply is unable to supply power but the second power supply is able to supply power.

16. The wearable device of claim 10,
wherein the first power supply harvests the first type of energy, and
wherein the second power supply harvests the second type of energy.

17. The wearable device of claim 10, wherein the first power supply harvests radio frequency (RF) radiation received at an antenna from an external reader and uses the harvested RF radiation to supply power to the wearable device.

18. The wearable device of claim 10, further comprising:
an antenna;
wherein the at least one sensor comprises an electrochemical sensor with a working electrode, a reference electrode, and a reagent that selectively reacts with an analyte; and
a transparent polymeric material mountable on an eye, and
wherein the electrochemical sensor, the antenna, the first power supply, the second power supply, and the controller are disposed within the transparent polymeric material.

19. The wearable device of claim 18, further comprising measurement electronics disposed within the transparent polymeric material that, when activated, apply a measurement voltage between the working electrode and the reference electrode, obtain a sensor measurement while the wearable device is exposed to a fluid, and use the antenna to transmit the sensor measurement.

20. The wearable device of claim 10, wherein the controller causes an external reader to reduce an amount of RF radiation transmitted to the wearable device in response to the determination that the second power supply is able to supply power.

21. A non-transitory computer readable medium (CRM) having instructions stored thereon that, when executed by one or more processors associated with a wearable device, cause the wearable device to perform operations, the operations comprising:
receiving a signal indicative of an availability of an auxiliary power supply to provide power to the wearable device, the wearable device including at least one sensor, a primary power supply and an auxiliary power supply; and
responsive to receiving the signal, operating the auxiliary power supply to supply power to the wearable device, wherein the primary power supply uses a first type of energy to power the wearable device and the auxiliary power supply uses a second type of energy to power the wearable device, wherein the first type of energy is different from the second type of energy.

22. The CRM of claim 21,
wherein the primary power supply harvests the first type of energy, and
wherein the auxiliary power supply harvests the second type of energy.

23. The CRM of claim 22,
wherein the primary power supply harvests radio frequency (RF) radiation received from an external reader and uses the harvested RF radiation to power the wearable device, and
wherein the operations further comprise responsive to receiving the signal, the wearable device causing the external reader to reduce an amount of RF radiation transmitted to the wearable device.

24. The CRM of claim 21, wherein the auxiliary power supply comprises a photovoltaic cell, the operations further comprising:
based on the received signal, determining that there is a threshold level of ambient light incident upon the photovoltaic cell, the threshold level of ambient light causing the photovoltaic cell to produce a voltage level sufficient to operate an auxiliary device associated with the wearable device.

25. The CRM of claim 21, wherein the auxiliary power supply comprises a charge storage device, the operations further comprising:
based on the received signal, determining that there is a threshold level of electric charge stored in the charge storage device, the threshold level of electric charge being sufficient to operate an auxiliary device associated with the wearable device.

26. The CRM of claim 21, wherein the at least one sensor comprises an electrochemical sensor with a working electrode, a reference electrode, and a reagent that selectively reacts with an analyte.

27. The CRM of claim 21, wherein the auxiliary power supply comprises a biofuel cell that generates electrical energy in response to a reaction between two catalysts present in tear fluid, the operations further comprising:
based on the received signal, determining that the biofuel cell is generating a threshold level of electrical energy, the threshold level being sufficient to operate an auxiliary device associated with the wearable device.

28. The CRM of claim 21,
wherein the signal is further indicative of an intention of the wearable device to operate an auxiliary device associated with the wearable device, the auxiliary device including one or more of a radio transmitter, an array of one or more light emitters, and a memory storage device, and
wherein the operations further comprise operating the auxiliary power supply to supply power to the auxiliary device.

29. The CRM of claim 21, wherein the operations further comprise:
supplying power from the primary power supply to an auxiliary device associated with the wearable device; and
responsive to receiving the signal, supplying additional power to the auxiliary device, the auxiliary device thereby receiving power from the primary power supply and the auxiliary power supply.

* * * * *